United States Patent [19]
Barry et al.

[11] Patent Number: 5,648,249
[45] Date of Patent: Jul. 15, 1997

[54] METHOD OF IMPROVING THE QUALITY OF STORED POTATOES

[75] Inventors: Gerard Francis Barry, St. Louis; Ganesh Murthy Kishore, Chesterfield; David Martin Stark, Fenton, all of Mo.; James Conrad Zalewski, Boise, Id.

[73] Assignee: Monsato Company, St. Louis, Mo.

[21] Appl. No.: 406,858

[22] PCT Filed: May 18, 1994

[86] PCT No.: PCT/US94/05275

§ 371 Date: Mar. 20, 1995

§ 102(e) Date: Mar. 20, 1995

[87] PCT Pub. No.: WO94/28149

PCT Pub. Date: Dec. 8, 1994

Related U.S. Application Data

[63] Continuation-in-part of Ser. No. 70,155, May 28, 1993, abandoned.

[51] Int. Cl.⁶ .......................... C12N 15/54; C12N 15/31; C12N 15/62; C12N 15/82

[52] U.S. Cl. ............. 435/172.3; 435/69.1; 435/69.7; 435/69.8; 435/70.1; 435/101; 435/194; 536/23.4; 536/23.7; 800/205; 800/DIG. 42

[58] Field of Search ............... 536/23.4, 23.6, 536/24.1, 23.7; 435/69.1, 69.7, 69.8, 172.3, 240.4, 70.1, 101, 194; 800/205, 255, DIG. 42

[56] References Cited

PUBLICATIONS

Anderson et al. 1990. pp. 159–180 In: Mol. Cell. Biol. Potato., Vayda et al., eds., C.A.B. International: Wallingford, U.K.

Meyer et al. 1993 Arch. Biochem. Biophys. 302(1):69–71.

*Primary Examiner*—David T. Fox
*Attorney, Agent, or Firm*—Grace L. Bonner

[57] ABSTRACT

The invention relates to a method of improving the quality of potatoes stored at reduced temperatures and a method of prolonging dormancy of stored potato tubers, by increasing the level of ADPglucose pyrophosphorylase enzyme activity within the potato tuber during storage at ambient or reduced temperatures. Novel DNA molecules, plant cells, and potato plants are provided which contain the gene for the ADPglucose pyrophosphorylase enzyme.

8 Claims, 2 Drawing Sheets

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
      ( A ) LENGTH: 1296 base pairs
      ( B ) TYPE: nucleic acid
      ( C ) STRANDEDNESS: double
      ( D ) TOPOLOGY: linear ( i i ) MOLECULE TYPE: DNA (genomic)

( i x ) FEATURE:
      ( A ) NAME/KEY: CDS
      ( B ) LOCATION: 1..1296

( x i ) SEQUENCE DESCRIPTION: SEQ ID NO:1:

```
ATG  GTT  AGT  TTA  GAG  AAG  AAC  GAT  CAC  TTA  ATG  TTG  GCG  CGC  CAG  CTG        48
Met  Val  Ser  Leu  Glu  Lys  Asn  Asp  His  Leu  Met  Leu  Ala  Arg  Gln  Leu
 1             5                        10                       15

CCA  TTG  AAA  TCT  GTT  GCC  CTG  ATA  CTG  GCG  GGA  GGA  CGT  GGT  ACC  CGC        96
Pro  Leu  Lys  Ser  Val  Ala  Leu  Ile  Leu  Ala  Gly  Gly  Arg  Gly  Thr  Arg
         20                       25                       30

CTG  AAG  GAT  TTA  ACC  AAT  AAG  CGA  GCA  AAA  CCG  GCC  GTA  CAC  TTC  GGC       144
Leu  Lys  Asp  Leu  Thr  Asn  Lys  Arg  Ala  Lys  Pro  Ala  Val  His  Phe  Gly
     35                       40                       45
```

| | | | | | | | | | | | | | | | | |
|---|---|---|---|---|---|---|---|---|---|---|---|---|---|---|---|---|
| GGT | AAG | TTC | CGC | ATT | ATC | GAC | TTT | GCG | CTG | TCT | AAC | TGC | ATC | AAC | TCC | 192 |
| Gly | Lys 50 | Phe | Arg | Ile | Ile | Asp 55 | Phe | Ala | Leu | Ser | Asn | Cys 60 | Ile | Asn | Ser | |
| GGG | ATC | CGT | CGT | ATG | GGC | GTG | ATC | ACC | CAG | TAC | CAG | TCC | CAC | ACT | CTG | 240 |
| Gly 65 | Ile | Arg | Arg | Met | Gly 70 | Val | Ile | Thr | Gln | Tyr 75 | Gln | Ser | His | Thr | Leu 80 | |
| GTG | CAG | CAC | ATT | CAG | CGC | GGC | TGG | TCA | TTC | TTC | AAT | GAA | GAA | ATG | AAC | 288 |
| Val | Gln | His | Ile | Gln 85 | Arg | Gly | Trp | Ser | Phe 90 | Phe | Asn | Glu | Glu | Met 95 | Asn | |
| GAG | TTT | GTC | GAT | CTG | CTG | CCA | GCA | CAG | CAG | AGA | ATG | AAA | GGG | GAA | AAC | 336 |
| Glu | Phe | Val | Asp 100 | Leu | Leu | Pro | Ala | Gln 105 | Gln | Arg | Met | Lys | Gly 110 | Glu | Asn | |
| TGG | TAT | CGC | GGC | ACC | GCA | GAT | GCG | GTC | ACC | CAA | AAC | CTC | GAC | ATT | ATC | 384 |
| Trp | Tyr | Arg 115 | Gly | Thr | Ala | Asp | Ala 120 | Val | Thr | Gln | Asn | Leu 125 | Asp | Ile | Ile | |
| CGT | CGT | TAT | AAA | GCG | GAA | TAC | GTG | GTG | ATC | CTG | GCG | GGC | GAC | CAT | ATC | 432 |
| Arg | Arg | Tyr 130 | Lys | Ala | Glu | Tyr | Val 135 | Val | Ile | Leu | Ala | Gly 140 | Asp | His | Ile | |
| TAC | AAG | CAA | GAC | TAC | TCG | CGT | ATG | CTT | ATC | GAT | CAC | GTC | GAA | AAA | GGT | 480 |
| Tyr | Lys 145 | Gln | Asp | Tyr | Ser | Arg 150 | Met | Leu | Ile | Asp | His 155 | Val | Glu | Lys | Gly 160 | |
| GTA | CGT | TGT | ACC | GTT | GTT | TGT | ATG | CCA | GTA | CCG | ATT | GAA | GAA | GCC | TCC | 528 |
| Val | Arg | Cys | Thr | Val 165 | Val | Cys | Met | Pro | Val 170 | Pro | Ile | Glu | Glu | Ala 175 | Ser | |
| GCA | TTT | GGC | GTT | ATG | GCG | GTT | GAT | GAG | AAC | GAT | AAA | ACT | ATC | GAA | TTC | 576 |
| Ala | Phe | Gly | Val | Met 180 | Ala | Val | Asp | Glu | Asn 185 | Asp | Lys | Thr | Ile | Glu 190 | Phe | |
| GTG | GAA | AAA | CCT | GCT | AAC | CCG | CCG | TCA | ATG | CCG | AAC | GAT | CCG | AGC | AAA | 624 |
| Val | Glu | Lys 195 | Pro | Ala | Asn | Pro | Pro 200 | Ser | Met | Pro | Asn | Asp 205 | Pro | Ser | Lys | |
| TCT | CTG | GCG | AGT | ATG | GGT | ATC | TAC | GTC | TTT | GAC | GCC | GAC | TAT | CTG | TAT | 672 |
| Ser | Leu 210 | Ala | Ser | Met | Gly | Ile 215 | Tyr | Val | Phe | Asp | Ala 220 | Asp | Tyr | Leu | Tyr | |
| GAA | CTG | CTG | GAA | GAA | GAC | GAT | CGC | GAT | GAG | AAC | TCC | AGC | CAC | GAC | TTT | 720 |
| Glu 225 | Leu | Leu | Glu | Glu | Asp 230 | Asp | Arg | Asp | Glu | Asn 235 | Ser | Ser | His | Asp | Phe 240 | |
| GGC | AAA | GAT | TTG | ATT | CCC | AAG | ATC | ACC | GAA | GCC | GGT | CTG | GCC | TAT | GCG | 768 |
| Gly | Lys | Asp | Leu | Ile 245 | Pro | Lys | Ile | Thr | Glu 250 | Ala | Gly | Leu | Ala | Tyr 255 | Ala | |
| CAC | CCG | TTC | CCG | CTC | TCT | TGC | GTA | CAA | TCC | GAC | CCG | GAT | GCC | GAG | CCG | 816 |
| His | Pro | Phe | Pro 260 | Leu | Ser | Cys | Val | Gln 265 | Ser | Asp | Pro | Asp | Ala 270 | Glu | Pro | |
| TAC | TGG | CGC | GAT | GTG | GGT | ACG | CTG | GAA | GCT | TAC | TGG | AAA | GCG | AAC | CTC | 864 |
| Tyr | Trp | Arg 275 | Asp | Val | Gly | Thr | Leu 280 | Glu | Ala | Tyr | Trp | Lys 285 | Ala | Asn | Leu | |
| GAT | CTG | GCC | TCT | GTG | GTG | CCG | AAA | CTG | GAT | ATG | TAC | GAT | CGC | AAT | TGG | 912 |
| Asp | Leu | Ala | Ser 290 | Val | Val | Pro | Lys | Leu 295 | Asp | Met | Tyr | Asp | Arg 300 | Asn | Trp | |
| CCA | ATT | CGC | ACC | TAC | AAT | GAA | TCA | TTA | CCG | CCA | GCG | AAA | TTC | GTG | CAG | 960 |
| Pro 305 | Ile | Arg | Thr | Tyr | Asn 310 | Glu | Ser | Leu | Pro | Pro 315 | Ala | Lys | Phe | Val | Gln 320 | |
| GAT | CGC | TCC | GGT | AGC | CAC | GGG | ATG | ACC | CTT | AAC | TCA | CTG | GTT | TCC | GGC | 1008 |
| Asp | Arg | Ser | Gly | Ser 325 | His | Gly | Met | Thr | Leu 330 | Asn | Ser | Leu | Val | Ser 335 | Gly | |
| GGT | TGT | GTG | ATC | TCC | GGT | TCG | GTG | GTG | GTG | CAG | TCC | GTT | CTG | TTC | TCG | 1056 |
| Gly | Cys | Val | Ile 340 | Ser | Gly | Ser | Val | Val 345 | Val | Gln | Ser | Val | Leu 350 | Phe | Ser | |
| CGC | GTT | CGC | GTG | AAT | TCA | TTC | TGC | AAC | ATT | GAT | TCC | GCC | GTA | TTG | TTA | 1104 |
| Arg | Val | Arg | Val | Asn 355 | Ser | Phe | Cys | Asn | Ile 360 | Asp | Ser | Ala | Val | Leu 365 | Leu | |

| | | | | | | | | | | | | | | | |
|---|---|---|---|---|---|---|---|---|---|---|---|---|---|---|---|
| CCG | GAA | GTA | TGG | GTA | GGT | CGC | TCG | TGC | CGT | CTG | CGC | CGC | TGC | GTC | ATC | 1152 |
| Pro | Glu | Val | Trp | Val | Gly | Arg | Ser | Cys | Arg | Leu | Arg | Arg | Cys | Val | Ile |
| 370 | | | | | 375 | | | | | 380 | | | | | |
| GAT | CGT | GCT | TGT | GTT | ATT | CCG | GAA | GGC | ATG | GTG | ATT | GGT | GAA | AAC | GCA | 1200 |
| Asp | Arg | Ala | Cys | Val | Ile | Pro | Glu | Gly | Met | Val | Ile | Gly | Glu | Asn | Ala |
| 385 | | | | 390 | | | | | 395 | | | | | 400 | |
| GAG | GAA | GAT | GCA | CGT | CGT | TTC | TAT | CGT | TCA | GAA | GAA | GGC | ATC | GTG | CTG | 1248 |
| Glu | Glu | Asp | Ala | Arg | Arg | Phe | Tyr | Arg | Ser | Glu | Glu | Gly | Ile | Val | Leu |
| | | | | 405 | | | | | 410 | | | | | 415 | |
| GTA | ACG | CGC | GAA | ATG | CTA | CGG | AAG | TTA | GGG | CAT | AAA | CAG | GAG | CGA | TAA | 1296 |
| Val | Thr | Arg | Glu | Met | Leu | Arg | Lys | Leu | Gly | His | Lys | Gln | Glu | Arg |
| | | | 420 | | | | | 425 | | | | | 430 | | |

( 2 ) INFORMATION FOR SEQ ID NO:2:

( i ) SEQUENCE CHARACTERISTICS:
        ( A ) LENGTH: 431 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Val | Ser | Leu | Glu | Lys | Asn | Asp | His | Leu | Met | Leu | Ala | Arg | Gln | Leu |
| 1 | | | | 5 | | | | | 10 | | | | | 15 | |
| Pro | Leu | Lys | Ser | Val | Ala | Leu | Ile | Leu | Ala | Gly | Gly | Arg | Gly | Thr | Arg |
| | | | 20 | | | | | 25 | | | | | 30 | | |
| Leu | Lys | Asp | Leu | Thr | Asn | Lys | Arg | Ala | Lys | Pro | Ala | Val | His | Phe | Gly |
| | | | 35 | | | | 40 | | | | | 45 | | | |
| Gly | Lys | Phe | Arg | Ile | Ile | Asp | Phe | Ala | Leu | Ser | Asn | Cys | Ile | Asn | Ser |
| | | 50 | | | | 55 | | | | | 60 | | | | |
| Gly | Ile | Arg | Arg | Met | Gly | Val | Ile | Thr | Gln | Tyr | Gln | Ser | His | Thr | Leu |
| 65 | | | | | 70 | | | | | 75 | | | | | 80 |
| Val | Gln | His | Ile | Gln | Arg | Gly | Trp | Ser | Phe | Phe | Asn | Glu | Glu | Met | Asn |
| | | | | 85 | | | | | 90 | | | | | 95 | |
| Glu | Phe | Val | Asp | Leu | Leu | Pro | Ala | Gln | Gln | Arg | Met | Lys | Gly | Glu | Asn |
| | | | 100 | | | | | 105 | | | | | 110 | | |
| Trp | Tyr | Arg | Gly | Thr | Ala | Asp | Ala | Val | Thr | Gln | Asn | Leu | Asp | Ile | Ile |
| | | 115 | | | | | 120 | | | | | 125 | | | |
| Arg | Arg | Tyr | Lys | Ala | Glu | Tyr | Val | Val | Ile | Leu | Ala | Gly | Asp | His | Ile |
| | 130 | | | | | 135 | | | | | 140 | | | | |
| Tyr | Lys | Gln | Asp | Tyr | Ser | Arg | Met | Leu | Ile | Asp | His | Val | Glu | Lys | Gly |
| 145 | | | | | 150 | | | | | 155 | | | | | 160 |
| Val | Arg | Cys | Thr | Val | Val | Cys | Met | Pro | Val | Pro | Ile | Glu | Glu | Ala | Ser |
| | | | | 165 | | | | | 170 | | | | | 175 | |
| Ala | Phe | Gly | Val | Met | Ala | Val | Asp | Glu | Asn | Asp | Lys | Thr | Ile | Glu | Phe |
| | | | 180 | | | | | 185 | | | | | 190 | | |
| Val | Glu | Lys | Pro | Ala | Asn | Pro | Pro | Ser | Met | Pro | Asn | Asp | Pro | Ser | Lys |
| | | 195 | | | | | 200 | | | | | 205 | | | |
| Ser | Leu | Ala | Ser | Met | Gly | Ile | Tyr | Val | Phe | Asp | Ala | Asp | Tyr | Leu | Tyr |
| | 210 | | | | | 215 | | | | | 220 | | | | |
| Glu | Leu | Leu | Glu | Glu | Asp | Asp | Arg | Asp | Glu | Asn | Ser | Ser | His | Asp | Phe |
| 225 | | | | | 230 | | | | | 235 | | | | | 240 |
| Gly | Lys | Asp | Leu | Ile | Pro | Lys | Ile | Thr | Glu | Ala | Gly | Leu | Ala | Tyr | Ala |
| | | | | 245 | | | | | 250 | | | | | 255 | |
| His | Pro | Phe | Pro | Leu | Ser | Cys | Val | Gln | Ser | Asp | Pro | Asp | Ala | Glu | Pro |
| | | | 260 | | | | | 265 | | | | | 270 | | |

```
Tyr Trp Arg Asp Val Gly Thr Leu Glu Ala Tyr Trp Lys Ala Asn Leu
        275                 280                 285

Asp Leu Ala Ser Val Val Pro Lys Leu Asp Met Tyr Asp Arg Asn Trp
        290                 295                 300

Pro Ile Arg Thr Tyr Asn Glu Ser Leu Pro Pro Ala Lys Phe Val Gln
305                 310                 315                 320

Asp Arg Ser Gly Ser His Gly Met Thr Leu Asn Ser Leu Val Ser Gly
                325                 330                 335

Gly Cys Val Ile Ser Gly Ser Val Val Gln Ser Val Leu Phe Ser
                340                 345                 350

Arg Val Arg Val Asn Ser Phe Cys Asn Ile Asp Ser Ala Val Leu Leu
        355                 360                 365

Pro Glu Val Trp Val Gly Arg Ser Cys Arg Leu Arg Arg Cys Val Ile
    370                 375                 380

Asp Arg Ala Cys Val Ile Pro Glu Gly Met Val Ile Gly Glu Asn Ala
385                 390                 395                 400

Glu Glu Asp Ala Arg Arg Phe Tyr Arg Ser Glu Glu Gly Ile Val Leu
                405                 410                 415

Val Thr Arg Glu Met Leu Arg Lys Leu Gly His Lys Gln Glu Arg
                420                 425                 430
```

(2) INFORMATION FOR SEQ ID NO:3:

( i ) SEQUENCE CHARACTERISTICS:
        ( A ) LENGTH: 1296 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1296

( x i ) SEQUENCE DESCRIPTION: SEQ ID NO:3:

```
ATG GTT AGT TTA GAG AAG AAC GAT CAC TTA ATG TTG GCG CGC CAG CTG        48
Met Val Ser Leu Glu Lys Asn Asp His Leu Met Leu Ala Arg Gln Leu
1               5                   10                  15

CCA TTG AAA TCT GTT GCC CTG ATA CTG GCG GGA GGA CGT GGT ACC CGC        96
Pro Leu Lys Ser Val Ala Leu Ile Leu Ala Gly Gly Arg Gly Thr Arg
            20                  25                  30

CTG AAG GAT TTA ACC AAT AAG CGA GCA AAA CCG GCC GTA CAC TTC GGC       144
Leu Lys Asp Leu Thr Asn Lys Arg Ala Lys Pro Ala Val His Phe Gly
        35                  40                  45

GGT AAG TTC CGC ATT ATC GAC TTT GCG CTG TCT AAC TGC ATC AAC TCC       192
Gly Lys Phe Arg Ile Ile Asp Phe Ala Leu Ser Asn Cys Ile Asn Ser
    50                  55                  60

GGG ATC CGT CGT ATG GGC GTG ATC ACC CAG TAC CAG TCC CAC ACT CTG       240
Gly Ile Arg Arg Met Gly Val Ile Thr Gln Tyr Gln Ser His Thr Leu
65                  70                  75                  80

GTG CAG CAC ATT CAG CGC GGC TGG TCA TTC TTC AAT GAA GAA ATG AAC       288
Val Gln His Ile Gln Arg Gly Trp Ser Phe Phe Asn Glu Glu Met Asn
                85                  90                  95

GAG TTT GTC GAT CTG CTG CCA GCA CAG CAG AGA ATG AAA GGG GAA AAC       336
Glu Phe Val Asp Leu Leu Pro Ala Gln Gln Arg Met Lys Gly Glu Asn
            100                 105                 110

TGG TAT CGC GGC ACC GCA GAT GCG GTC ACC CAA AAC CTC GAC ATT ATC       384
Trp Tyr Arg Gly Thr Ala Asp Ala Val Thr Gln Asn Leu Asp Ile Ile
        115                 120                 125

CGT CGT TAT AAA GCG GAA TAC GTG GTG ATC CTG GCG GGC GAC CAT ATC       432
```

```
Arg Arg Tyr Lys Ala Glu Tyr Val Val Ile Leu Ala Gly Asp His Ile
    130             135                 140

TAC AAG CAA GAC TAC TCG CGT ATG CTT ATC GAT CAC GTC GAA AAA GGT      480
Tyr Lys Gln Asp Tyr Ser Arg Met Leu Ile Asp His Val Glu Lys Gly
145             150                 155                 160

GTA CGT TGT ACC GTT GTT TGT ATG CCA GTA CCG ATT GAA GAA GCC TCC      528
Val Arg Cys Thr Val Val Cys Met Pro Val Pro Ile Glu Glu Ala Ser
                165                 170                 175

GCA TTT GGC GTT ATG GCG GTT GAT GAG AAC GAT AAA ACT ATC GAA TTC      576
Ala Phe Gly Val Met Ala Val Asp Glu Asn Asp Lys Thr Ile Glu Phe
            180                 185                 190

GTG GAA AAA CCT GCT AAC CCG CCG TCA ATG CCG AAC GAT CCG AGC AAA      624
Val Glu Lys Pro Ala Asn Pro Pro Ser Met Pro Asn Asp Pro Ser Lys
        195                 200                 205

TCT CTG GCG AGT ATG GGT ATC TAC GTC TTT GAC GCC GAT TAT CTG TAT      672
Ser Leu Ala Ser Met Gly Ile Tyr Val Phe Asp Ala Asp Tyr Leu Tyr
    210                 215                 220

GAA CTG CTG GAA GAA GAC GAT CGC GAT GAG AAC TCC AGC CAC GAC TTT      720
Glu Leu Leu Glu Glu Asp Asp Arg Asp Glu Asn Ser Ser His Asp Phe
225             230                 235                 240

GGC AAA GAT TTG ATT CCC AAG ATC ACC GAA GCC GGT CTG GCC TAT GCG      768
Gly Lys Asp Leu Ile Pro Lys Ile Thr Glu Ala Gly Leu Ala Tyr Ala
            245                 250                 255

CAC CCG TTC CCG CTC TCT TGC GTA CAA TCC GAC CCG GAT GCC GAG CCG      816
His Pro Phe Pro Leu Ser Cys Val Gln Ser Asp Pro Asp Ala Glu Pro
        260                 265                 270

TAC TGG CGC GAT GTG GGT ACG CTG GAA GCT TAC TGG AAA GCG AAC CTC      864
Tyr Trp Arg Asp Val Gly Thr Leu Glu Ala Tyr Trp Lys Ala Asn Leu
    275                 280                 285

GAT CTG GCC TCT GTG GTG CCG GAA CTG GAT ATG TAC GAT CGC AAT TGG      912
Asp Leu Ala Ser Val Val Pro Glu Leu Asp Met Tyr Asp Arg Asn Trp
290             295                 300

CCA ATT CGC ACC TAC AAT GAA TCA TTA CCG CCA GCG AAA TTC GTG CAG      960
Pro Ile Arg Thr Tyr Asn Glu Ser Leu Pro Pro Ala Lys Phe Val Gln
305             310                 315                 320

GAT CGC TCC GGT AGC CAC GGG ATG ACC CTT AAC TCA CTG GTT TCC GAC     1008
Asp Arg Ser Gly Ser His Gly Met Thr Leu Asn Ser Leu Val Ser Asp
                325                 330                 335

GGT TGT GTG ATC TCC GGT TCG GTG GTG GTG CAG TCC GTT CTG TTC TCG     1056
Gly Cys Val Ile Ser Gly Ser Val Val Val Gln Ser Val Leu Phe Ser
            340                 345                 350

CGC GTT CGC GTG AAT TCA TTC TGC AAC ATT GAT TCC GCC GTA TTG TTA     1104
Arg Val Arg Val Asn Ser Phe Cys Asn Ile Asp Ser Ala Val Leu Leu
        355                 360                 365

CCG GAA GTA TGG GTA GGT CGC TCG TGC CGT CTG CGC CGC TGC GTC ATC     1152
Pro Glu Val Trp Val Gly Arg Ser Cys Arg Leu Arg Arg Cys Val Ile
    370                 375                 380

GAT CGT GCT TGT GTT ATT CCG GAA GGC ATG GTG ATT GGT GAA AAC GCA     1200
Asp Arg Ala Cys Val Ile Pro Glu Gly Met Val Ile Gly Glu Asn Ala
385             390                 395                 400

GAG GAA GAT GCA CGT CGT TTC TAT CGT TCA GAA GAA GGC ATC GTG CTG     1248
Glu Glu Asp Ala Arg Arg Phe Tyr Arg Ser Glu Glu Gly Ile Val Leu
            405                 410                 415

GTA ACG CGC GAA ATG CTA CGG AAG TTA GGG CAT AAA CAG GAG CGA TAA     1296
Val Thr Arg Glu Met Leu Arg Lys Leu Gly His Lys Gln Glu Arg
        420                 425                 430
```

( 2 ) INFORMATION FOR SEQ ID NO:4:

( i ) SEQUENCE CHARACTERISTICS:
        ( A ) LENGTH: 431 amino acids (B) TYPE: amino acid
(D) TOPOLOGY: linear (ii) MOLECULE TYPE: protein (xi) SEQUENCE DESCRIPTION: SEQ ID NO:4:

```
Met Val Ser Leu Glu Lys Asn Asp His Leu Met Leu Ala Arg Gln Leu
 1               5                  10                  15

Pro Leu Lys Ser Val Ala Leu Ile Leu Ala Gly Gly Arg Gly Thr Arg
            20                  25                  30

Leu Lys Asp Leu Thr Asn Lys Arg Ala Lys Pro Ala Val His Phe Gly
        35                  40                  45

Gly Lys Phe Arg Ile Ile Asp Phe Ala Leu Ser Asn Cys Ile Asn Ser
    50                  55                  60

Gly Ile Arg Arg Met Gly Val Ile Thr Gln Tyr Gln Ser His Thr Leu
65                  70                  75                  80

Val Gln His Ile Gln Arg Gly Trp Ser Phe Phe Asn Glu Glu Met Asn
                85                  90                  95

Glu Phe Val Asp Leu Leu Pro Ala Gln Gln Arg Met Lys Gly Glu Asn
            100                 105                 110

Trp Tyr Arg Gly Thr Ala Asp Ala Val Thr Gln Asn Leu Asp Ile Ile
        115                 120                 125

Arg Arg Tyr Lys Ala Glu Tyr Val Val Ile Leu Ala Gly Asp His Ile
130                 135                 140

Tyr Lys Gln Asp Tyr Ser Arg Met Leu Ile Asp His Val Glu Lys Gly
145                 150                 155                 160

Val Arg Cys Thr Val Val Cys Met Pro Val Pro Ile Glu Glu Ala Ser
                165                 170                 175

Ala Phe Gly Val Met Ala Val Asp Glu Asn Asp Lys Thr Ile Glu Phe
            180                 185                 190

Val Glu Lys Pro Ala Asn Pro Pro Ser Met Pro Asn Asp Pro Ser Lys
        195                 200                 205

Ser Leu Ala Ser Met Gly Ile Tyr Val Phe Asp Ala Asp Tyr Leu Tyr
    210                 215                 220

Glu Leu Leu Glu Glu Asp Asp Arg Asp Glu Asn Ser Ser His Asp Phe
225                 230                 235                 240

Gly Lys Asp Leu Ile Pro Lys Ile Thr Glu Ala Gly Leu Ala Tyr Ala
                245                 250                 255

His Pro Phe Pro Leu Ser Cys Val Gln Ser Asp Pro Asp Ala Glu Pro
            260                 265                 270

Tyr Trp Arg Asp Val Gly Thr Leu Glu Ala Tyr Trp Lys Ala Asn Leu
        275                 280                 285

Asp Leu Ala Ser Val Val Pro Glu Leu Asp Met Tyr Asp Arg Asn Trp
290                 295                 300

Pro Ile Arg Thr Tyr Asn Glu Ser Leu Pro Pro Ala Lys Phe Val Gln
305                 310                 315                 320

Asp Arg Ser Gly Ser His Gly Met Thr Leu Asn Ser Leu Val Ser Asp
                325                 330                 335

Gly Cys Val Ile Ser Gly Ser Val Val Val Gln Ser Val Leu Phe Ser
            340                 345                 350

Arg Val Arg Val Asn Ser Phe Cys Asn Ile Asp Ser Ala Val Leu Leu
        355                 360                 365

Pro Glu Val Trp Val Gly Arg Ser Cys Arg Leu Arg Arg Cys Val Ile
370                 375                 380

Asp Arg Ala Cys Val Ile Pro Glu Gly Met Val Ile Gly Glu Asn Ala
```

```
                385                    390                    395                    400
Glu  Glu  Asp  Ala  Arg  Arg  Phe  Tyr  Arg  Ser  Glu  Glu  Gly  Ile  Val  Leu
                     405                         410                       415

Val  Thr  Arg  Glu  Met  Leu  Arg  Lys  Leu  Gly  His  Lys  Gln  Glu  Arg
                420                       425                    430
```

(2) INFORMATION FOR SEQ ID NO:5:

(i) SEQUENCE CHARACTERISTICS:
        (A) LENGTH: 355 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 88..354

(xi) SEQUENCE DESCRIPTION: SEQ ID NO:5:

```
AAGCTTGTTC TCATTGTTGT TATCATTATA TATAGATGAC CAAAGCACTA GACCAAACCT        60

CAGTCACACA AAGAGTAAAG AAGAACA ATG GCT TCC TCT ATG CTC TCT TCC          111
                             Met Ala Ser Ser Met Leu Ser Ser
                              1               5

GCT  ACT  ATG  GTT  GCC  TCT  CCG  GCT  CAG  GCC  ACT  ATG  GTC  GCT  CCT  TTC    159
Ala  Thr  Met  Val  Ala  Ser  Pro  Ala  Gln  Ala  Thr  Met  Val  Ala  Pro  Phe
          10                       15                      20

AAC  GGA  CTT  AAG  TCC  TCC  GCT  GCC  TTC  CCA  GCC  ACC  CGC  AAG  GCT  AAC    207
Asn  Gly  Leu  Lys  Ser  Ser  Ala  Ala  Phe  Pro  Ala  Thr  Arg  Lys  Ala  Asn
25                       30                       35                       40

AAC  GAC  ATT  ACT  TCC  ATC  ACA  AGC  AAC  GGC  GGA  AGA  GTT  AAC  TGC  ATG    255
Asn  Asp  Ile  Thr  Ser  Ile  Thr  Ser  Asn  Gly  Gly  Arg  Val  Asn  Cys  Met
                    45                       50                       55

CAG  GTG  TGG  CCT  CCG  ATT  GGA  AAG  AAG  AAG  TTT  GAG  ACT  CTC  TCT  TAC    303
Gln  Val  Trp  Pro  Pro  Ile  Gly  Lys  Lys  Lys  Phe  Glu  Thr  Leu  Ser  Tyr
               60                       65                       70

CTT  CCT  GAC  CTT  ACC  GAT  TCC  GGT  GGT  CGC  GTC  AAC  TGC  ATG  CAG  GCC    351
Leu  Pro  Asp  Leu  Thr  Asp  Ser  Gly  Gly  Arg  Val  Asn  Cys  Met  Gln  Ala
          75                       80                       85

ATG  G                                                                    355
Met
```

(2) INFORMATION FOR SEQ ID NO:6:

(i) SEQUENCE CHARACTERISTICS:
        (A) LENGTH: 89 amino acids
        (B) TYPE: amino acid
        (D) TOPOLOGY: linear (ii) MOLECULE TYPE: protein (xi) SEQUENCE DESCRIPTION: SEQ ID NO:6:

```
Met  Ala  Ser  Ser  Met  Leu  Ser  Ser  Ala  Thr  Met  Val  Ala  Ser  Pro  Ala
 1                    5                       10                      15

Gln  Ala  Thr  Met  Val  Ala  Pro  Phe  Asn  Gly  Leu  Lys  Ser  Ser  Ala  Ala
               20                       25                       30

Phe  Pro  Ala  Thr  Arg  Lys  Ala  Asn  Asn  Asp  Ile  Thr  Ser  Ile  Thr  Ser
          35                       40                       45

Asn  Gly  Gly  Arg  Val  Asn  Cys  Met  Gln  Val  Trp  Pro  Pro  Ile  Gly  Lys
          50                       55                       60

Lys  Lys  Phe  Glu  Thr  Leu  Ser  Tyr  Leu  Pro  Asp  Leu  Thr  Asp  Ser  Gly
```

|    |    |    |    |    | 65 |    |    |    |    | 70 |    |    |    |    | 75 |    |    |    |    | 80 |
|----|----|----|----|----|----|----|----|----|----|----|----|----|----|----|----|----|----|----|----|----|

Gly Arg Val Asn Cys Met Gln Ala Met
                    85

(2) INFORMATION FOR SEQ ID NO:7:

(i) SEQUENCE CHARACTERISTICS:
        (A) LENGTH: 1575 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 3..1565

(xi) SEQUENCE DESCRIPTION: SEQ ID NO:7:

```
CC ATG GCG GCT TCC ATT GGA GCC TTA AAA TCT TCA CCT TCT TCT AAC         47
   Met Ala Ala Ser Ile Gly Ala Leu Lys Ser Ser Pro Ser Ser Asn
   1               5                  10                  15

AAT TGC ATC AAT GAG AGA AGA AAT GAT TCT ACA CGT GCT GTA TCC AGC         95
Asn Cys Ile Asn Glu Arg Arg Asn Asp Ser Thr Arg Ala Val Ser Ser
                20                  25                  30

AGA AAT CTC TCA TTT TCG TCT TCT CAT CTC GCC GGA GAC AAG TTG ATG        143
Arg Asn Leu Ser Phe Ser Ser Ser His Leu Ala Gly Asp Lys Leu Met
            35                  40                  45

CCT GTA TCG TCC TTA CGT TCC CAA GGA GTC CGA TTC AAT GTG AGA AGA        191
Pro Val Ser Ser Leu Arg Ser Gln Gly Val Arg Phe Asn Val Arg Arg
        50                  55                  60

AGT CCA ATG ATT GTG TCG CCA AAG GCT GTT TCT GAT TCG CAG AAT TCA        239
Ser Pro Met Ile Val Ser Pro Lys Ala Val Ser Asp Ser Gln Asn Ser
    65                  70                  75

CAG ACA TGT CTA GAC CCA GAT GCT AGC CGG AGT GTT TTG GGA ATT ATT        287
Gln Thr Cys Leu Asp Pro Asp Ala Ser Arg Ser Val Leu Gly Ile Ile
80                  85                  90                  95

CTT GGA GGT GGA GCT GGG ACC CGA CTT TAT CCT CTA ACT AAA AAA AGA        335
Leu Gly Gly Gly Ala Gly Thr Arg Leu Tyr Pro Leu Thr Lys Lys Arg
                100                 105                 110

GCA AAG CCA GCT GTT CCA CTT GGA GCA AAT TAT CGT CTG ATT GAC ATT        383
Ala Lys Pro Ala Val Pro Leu Gly Ala Asn Tyr Arg Leu Ile Asp Ile
            115                 120                 125

CCT GTA AGC AAC TGC TTG AAC AGT AAT ATA TCC AAG ATT TAT GTT CTC        431
Pro Val Ser Asn Cys Leu Asn Ser Asn Ile Ser Lys Ile Tyr Val Leu
        130                 135                 140

ACA CAA TTC AAC TCT GCC TCT CTG AAT CGC CAC CTT TCA CGA GCA TAT        479
Thr Gln Phe Asn Ser Ala Ser Leu Asn Arg His Leu Ser Arg Ala Tyr
    145                 150                 155

GCT AGC AAC ATG GGA GGA TAC AAA AAC GAG GGC TTT GTG GAA GTT CTT        527
Ala Ser Asn Met Gly Gly Tyr Lys Asn Glu Gly Phe Val Glu Val Leu
160                 165                 170                 175

GCT GCT CAA CAA AGT CCA GAG AAC CCC GAT TGG TTC CAG GGC ACG GCT        575
Ala Ala Gln Gln Ser Pro Glu Asn Pro Asp Trp Phe Gln Gly Thr Ala
                180                 185                 190

GAT GCT GTC AGA CAA TAT CTG TGG TTG TTT GAG GAG CAT ACT GTT CTT        623
Asp Ala Val Arg Gln Tyr Leu Trp Leu Phe Glu Glu His Thr Val Leu
            195                 200                 205

GAA TAC CTT ATA CTT GCT GGA GAT CAT CTG TAT CGA ATG GAT TAT GAA        671
Glu Tyr Leu Ile Leu Ala Gly Asp His Leu Tyr Arg Met Asp Tyr Glu
        210                 215                 220

AAG TTT ATT CAA GCC CAC AGA GAA ACA GAT GCT GAT ATT ACC GTT GCC        719
```

-continued

```
          Lys Phe Ile Gln Ala His Arg Glu Thr Asp Ala Asp Ile Thr Val Ala
              225                 230                 235

GCA CTG CCA ATG GAC GAG AAG CGT GCC ACT GCA TTC GGT CTC ATG AAG                767
Ala Leu Pro Met Asp Glu Lys Arg Ala Thr Ala Phe Gly Leu Met Lys
240                 245                 250                 255

ATT GAC GAA GAA GGA CGC ATT ATT GAA TTT GCA GAG AAA CCG CAA GGA                815
Ile Asp Glu Glu Gly Arg Ile Ile Glu Phe Ala Glu Lys Pro Gln Gly
                        260                 265                 270

GAG CAA TTG CAA GCA ATG AAA GTG GAT ACT ACC ATT TTA GGT CTT GAT                863
Glu Gln Leu Gln Ala Met Lys Val Asp Thr Thr Ile Leu Gly Leu Asp
                275                 280                 285

GAC AAG AGA GCT AAA GAA ATG CCT TTC ATT GCC AGT ATG GGT ATA TAT                911
Asp Lys Arg Ala Lys Glu Met Pro Phe Ile Ala Ser Met Gly Ile Tyr
        290                 295                 300

GTC ATT AGC AAA GAC GTG ATG TTA AAC CTA CTT CGT GAC AAG TTC CCT                959
Val Ile Ser Lys Asp Val Met Leu Asn Leu Leu Arg Asp Lys Phe Pro
    305                 310                 315

GGG GCC AAT GAT TTT GGT AGT GAA GTT ATT CCT GGT GCA ACT TCA CTT                1007
Gly Ala Asn Asp Phe Gly Ser Glu Val Ile Pro Gly Ala Thr Ser Leu
320                 325                 330                 335

GGG ATG AGA GTG CAA GCT TAT TTA TAT GAT GGG TAC TGG GAA GAT ATT                1055
Gly Met Arg Val Gln Ala Tyr Leu Tyr Asp Gly Tyr Trp Glu Asp Ile
                        340                 345                 350

GGT ACC ATT GAA GCT TTC TAC AAT GCC AAT TTG GGC ATT ACA AAA AAG                1103
Gly Thr Ile Glu Ala Phe Tyr Asn Ala Asn Leu Gly Ile Thr Lys Lys
                355                 360                 365

CCG GTG CCA GAT TTT AGC TTT TAC GAC CGA TCA GCC CCA ATC TAC ACC                1151
Pro Val Pro Asp Phe Ser Phe Tyr Asp Arg Ser Ala Pro Ile Tyr Thr
        370                 375                 380

CAA CCT CGA TAT CTA CCA CCA TCA AAA ATG CTT GAT GCT GAT GTC ACA                1199
Gln Pro Arg Tyr Leu Pro Pro Ser Lys Met Leu Asp Ala Asp Val Thr
    385                 390                 395

GAT AGT GTC ATT GGT GAA GGT TGT GTG ATC AAG AAC TGT AAG ATT CAT                1247
Asp Ser Val Ile Gly Glu Gly Cys Val Ile Lys Asn Cys Lys Ile His
400                 405                 410                 415

CAT TCC GTG GTT GGA CTC AGA TCA TGC ATA TCA GAG GGA GCA ATT ATA                1295
His Ser Val Val Gly Leu Arg Ser Cys Ile Ser Glu Gly Ala Ile Ile
                        420                 425                 430

GAA GAC TCA CTT TTG ATG GGG GCA GAT TAC TAT GAG ACT GAT GCT GAC                1343
Glu Asp Ser Leu Leu Met Gly Ala Asp Tyr Tyr Glu Thr Asp Ala Asp
                435                 440                 445

AGG AAG TTG CTG GCT GCA AAG GGC AGT GTC CCA ATT GGC ATC GGC AAG                1391
Arg Lys Leu Leu Ala Ala Lys Gly Ser Val Pro Ile Gly Ile Gly Lys
        450                 455                 460

AAT TGT CAC ATT AAA AGA GCC ATT ATC GAC AAG AAT GCC CGT ATA GGG                1439
Asn Cys His Ile Lys Arg Ala Ile Ile Asp Lys Asn Ala Arg Ile Gly
    465                 470                 475

GAC AAT GTG AAG ATC ATT AAC AAA GAC AAC GTT CAA GAA GCG GCT AGG                1487
Asp Asn Val Lys Ile Ile Asn Lys Asp Asn Val Gln Glu Ala Ala Arg
480                 485                 490                 495

GAA ACA GAT GGA TAC TTC ATC AAG AGT GGG ATT GTC ACC GTC ATC AAG                1535
Glu Thr Asp Gly Tyr Phe Ile Lys Ser Gly Ile Val Thr Val Ile Lys
                        500                 505                 510

GAT GCT TTG ATT CCA AGT GGA ATC ATC ATC TGATGAGCTC                             1575
Asp Ala Leu Ile Pro Ser Gly Ile Ile Ile
                515                 520
```

( 2 ) INFORMATION FOR SEQ ID NO:8:

( i ) SEQUENCE CHARACTERISTICS:
        ( A ) LENGTH: 521 amino acids (B) TYPE: amino acid
(D) TOPOLOGY: linear (ii) MOLECULE TYPE: protein (xi) SEQUENCE DESCRIPTION: SEQ ID NO:8:

```
Met  Ala  Ala  Ser  Ile  Gly  Ala  Leu  Lys  Ser  Ser  Pro  Ser  Ser  Asn
 1              5                        10                       15

Cys  Ile  Asn  Glu  Arg  Arg  Asn  Asp  Ser  Thr  Arg  Ala  Val  Ser  Arg
              20                        25                       30

Asn  Leu  Ser  Phe  Ser  Ser  Ser  His  Leu  Ala  Gly  Asp  Lys  Leu  Met  Pro
              35                        40                       45

Val  Ser  Ser  Leu  Arg  Ser  Gln  Gly  Val  Arg  Phe  Asn  Val  Arg  Arg  Ser
              50                        55                       60

Pro  Met  Ile  Val  Ser  Pro  Lys  Ala  Val  Ser  Asp  Ser  Gln  Asn  Ser  Gln
 65                       70                        75                       80

Thr  Cys  Leu  Asp  Pro  Asp  Ala  Ser  Arg  Ser  Val  Leu  Gly  Ile  Ile  Leu
                    85                        90                       95

Gly  Gly  Gly  Ala  Gly  Thr  Arg  Leu  Tyr  Pro  Leu  Thr  Lys  Lys  Arg  Ala
              100                       105                      110

Lys  Pro  Ala  Val  Pro  Leu  Gly  Ala  Asn  Tyr  Arg  Leu  Ile  Asp  Ile  Pro
              115                       120                      125

Val  Ser  Asn  Cys  Leu  Asn  Ser  Asn  Ile  Ser  Lys  Ile  Tyr  Val  Leu  Thr
     130                       135                      140

Gln  Phe  Asn  Ser  Ala  Ser  Leu  Asn  Arg  His  Leu  Ser  Arg  Ala  Tyr  Ala
145                      150                       155                      160

Ser  Asn  Met  Gly  Gly  Tyr  Lys  Asn  Glu  Gly  Phe  Val  Glu  Val  Leu  Ala
                    165                       170                      175

Ala  Gln  Gln  Ser  Pro  Glu  Asn  Pro  Asp  Trp  Phe  Gln  Gly  Thr  Ala  Asp
               180                       185                      190

Ala  Val  Arg  Gln  Tyr  Leu  Trp  Leu  Phe  Glu  Glu  His  Thr  Val  Leu  Glu
          195                       200                      205

Tyr  Leu  Ile  Leu  Ala  Gly  Asp  His  Leu  Tyr  Arg  Met  Asp  Tyr  Glu  Lys
     210                       215                      220

Phe  Ile  Gln  Ala  His  Arg  Glu  Thr  Asp  Ala  Asp  Ile  Thr  Val  Ala  Ala
225                      230                       235                      240

Leu  Pro  Met  Asp  Glu  Lys  Arg  Ala  Thr  Ala  Phe  Gly  Leu  Met  Lys  Ile
                    245                       250                      255

Asp  Glu  Glu  Gly  Arg  Ile  Ile  Glu  Phe  Ala  Glu  Lys  Pro  Gln  Gly  Glu
               260                       265                      270

Gln  Leu  Gln  Ala  Met  Lys  Val  Asp  Thr  Thr  Ile  Leu  Gly  Leu  Asp  Asp
          275                       280                      285

Lys  Arg  Ala  Lys  Glu  Met  Pro  Phe  Ile  Ala  Ser  Met  Gly  Ile  Tyr  Val
     290                       295                      300

Ile  Ser  Lys  Asp  Val  Met  Leu  Asn  Leu  Leu  Arg  Asp  Lys  Phe  Pro  Gly
305                      310                       315                      320

Ala  Asn  Asp  Phe  Gly  Ser  Glu  Val  Ile  Pro  Gly  Ala  Thr  Ser  Leu  Gly
               325                       330                      335

Met  Arg  Val  Gln  Ala  Tyr  Leu  Tyr  Asp  Gly  Tyr  Trp  Glu  Asp  Ile  Gly
          340                       345                      350

Thr  Ile  Glu  Ala  Phe  Tyr  Asn  Ala  Asn  Leu  Gly  Ile  Thr  Lys  Lys  Pro
     355                       360                      365

Val  Pro  Asp  Phe  Ser  Phe  Tyr  Asp  Arg  Ser  Ala  Pro  Ile  Tyr  Thr  Gln
370                      375                       380

Pro  Arg  Tyr  Leu  Pro  Pro  Ser  Lys  Met  Leu  Asp  Ala  Asp  Val  Thr  Asp
```

```
385                          390                          395                          400
Ser  Val  Ile  Gly  Glu  Gly  Cys  Val  Ile  Lys  Asn  Cys  Lys  Ile  His  His
                    405                           410                          415

Ser  Val  Val  Gly  Leu  Arg  Ser  Cys  Ile  Ser  Glu  Gly  Ala  Ile  Ile  Glu
               420                           425                           430

Asp  Ser  Leu  Leu  Met  Gly  Ala  Asp  Tyr  Tyr  Glu  Thr  Asp  Ala  Asp  Arg
               435                           440                           445

Lys  Leu  Leu  Ala  Ala  Lys  Gly  Ser  Val  Pro  Ile  Gly  Ile  Gly  Lys  Asn
     450                           455                           460

Cys  His  Ile  Lys  Arg  Ala  Ile  Ile  Asp  Lys  Asn  Ala  Arg  Ile  Gly  Asp
465                      470                           475                           480

Asn  Val  Lys  Ile  Ile  Asn  Lys  Asp  Asn  Val  Gln  Glu  Ala  Ala  Arg  Glu
                    485                           490                           495

Thr  Asp  Gly  Tyr  Phe  Ile  Lys  Ser  Gly  Ile  Val  Thr  Val  Ile  Lys  Asp
               500                           505                           510

Ala  Leu  Ile  Pro  Ser  Gly  Ile  Ile  Ile
               515                 520
```

( 2 ) INFORMATION FOR SEQ ID NO:9:

( i ) SEQUENCE CHARACTERISTICS:
        ( A ) LENGTH: 1519 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..1410

( x i ) SEQUENCE DESCRIPTION: SEQ ID NO:9:

```
AAC  AAG  ATC  AAA  CCT  GGG  GTT  GCT  TAC  TCT  GTG  ATC  ACT  ACT  GAA  AAT       48
Asn  Lys  Ile  Lys  Pro  Gly  Val  Ala  Tyr  Ser  Val  Ile  Thr  Thr  Glu  Asn
  1                 5                          10                          15

GAC  ACA  CAG  ACT  GTG  TTC  GTA  GAT  ATG  CCA  CGT  CTT  GAG  AGA  CGC  CGG       96
Asp  Thr  Gln  Thr  Val  Phe  Val  Asp  Met  Pro  Arg  Leu  Glu  Arg  Arg  Arg
                    20                          25                          30

GCA  AAT  CCA  AAG  GAT  GTG  GCT  GCA  GTC  ATA  CTG  GGA  GGA  GGA  GAA  GGG      144
Ala  Asn  Pro  Lys  Asp  Val  Ala  Ala  Val  Ile  Leu  Gly  Gly  Gly  Glu  Gly
               35                          40                          45

ACC  AAG  TTA  TTC  CCA  CTT  ACA  AGT  AGA  ACT  GCA  ACC  CCT  GCT  GTT  CCG      192
Thr  Lys  Leu  Phe  Pro  Leu  Thr  Ser  Arg  Thr  Ala  Thr  Pro  Ala  Val  Pro
     50                          55                          60

GTT  GGA  GGA  TGC  TAC  AGG  CTA  ATA  GAC  ATC  CCA  ATG  AGC  AAC  TGT  ATC      240
Val  Gly  Gly  Cys  Tyr  Arg  Leu  Ile  Asp  Ile  Pro  Met  Ser  Asn  Cys  Ile
65                       70                          75                          80

AAC  AGT  GCT  ATT  AAC  AAG  ATT  TTT  GTG  CTG  ACA  CAG  TAC  AAT  TCT  GCT      288
Asn  Ser  Ala  Ile  Asn  Lys  Ile  Phe  Val  Leu  Thr  Gln  Tyr  Asn  Ser  Ala
                    85                          90                          95

CCC  CTG  AAT  CGT  CAC  ATT  GCT  CGA  ACA  TAT  TTT  GGC  AAT  GGT  GTG  AGC      336
Pro  Leu  Asn  Arg  His  Ile  Ala  Arg  Thr  Tyr  Phe  Gly  Asn  Gly  Val  Ser
               100                         105                         110

TTT  GGA  GAT  GGA  TTT  GTC  GAG  GTA  CTA  GCT  GCA  ACT  CAG  ACA  CCC  GGG      384
Phe  Gly  Asp  Gly  Phe  Val  Glu  Val  Leu  Ala  Ala  Thr  Gln  Thr  Pro  Gly
               115                         120                         125

GAA  GCA  GGA  AAA  AAA  TGG  TTT  CAA  GGA  ACA  GCA  GAT  GCT  GTT  AGA  AAA      432
Glu  Ala  Gly  Lys  Lys  Trp  Phe  Gln  Gly  Thr  Ala  Asp  Ala  Val  Arg  Lys
               130                         135                         140

TTT  ATA  TGG  GTT  TTT  GAG  GAC  GCT  AAG  AAC  AAG  AAT  ATT  GAA  AAT  ATC      480
```

| | | | | | | | | | | | | | | | | |
|---|---|---|---|---|---|---|---|---|---|---|---|---|---|---|---|---|
| Phe | Ile | Trp | Val | Phe | Glu | Asp | Ala | Lys | Asn | Lys | Asn | Ile | Glu | Asn | Ile | |
| 145 | | | | 150 | | | | | 155 | | | | | | 160 | |

| GTT | GTA | CTA | TCT | GGG | GAT | CAT | CTT | TAT | AGG | ATG | GAT | TAT | ATG | GAG | TTG | 528 |
|---|---|---|---|---|---|---|---|---|---|---|---|---|---|---|---|---|
| Val | Val | Leu | Ser | Gly | Asp | His | Leu | Tyr | Arg | Met | Asp | Tyr | Met | Glu | Leu | |
| | | | | 165 | | | | | 170 | | | | | 175 | | |

| GTG | CAG | AAC | CAT | ATT | GAC | AGG | AAT | GCT | GAT | ATT | ACT | CTT | TCA | TGT | GCA | 576 |
|---|---|---|---|---|---|---|---|---|---|---|---|---|---|---|---|---|
| Val | Gln | Asn | His | Ile | Asp | Arg | Asn | Ala | Asp | Ile | Thr | Leu | Ser | Cys | Ala | |
| | | | 180 | | | | | 185 | | | | | 190 | | | |

| CCA | GCT | GAG | GAC | AGC | CGA | GCA | TCA | GAT | TTT | GGG | CTG | GTC | AAG | ATT | GAC | 624 |
|---|---|---|---|---|---|---|---|---|---|---|---|---|---|---|---|---|
| Pro | Ala | Glu | Asp | Ser | Arg | Ala | Ser | Asp | Phe | Gly | Leu | Val | Lys | Ile | Asp | |
| | | 195 | | | | | 200 | | | | | 205 | | | | |

| AGC | AGA | GGC | AGA | GTA | GTC | CAG | TTT | GCT | GAA | AAA | CCA | AAA | GGT | TTT | GAT | 672 |
|---|---|---|---|---|---|---|---|---|---|---|---|---|---|---|---|---|
| Ser | Arg | Gly | Arg | Val | Val | Gln | Phe | Ala | Glu | Lys | Pro | Lys | Gly | Phe | Asp | |
| | 210 | | | | | 215 | | | | | 220 | | | | | |

| CTT | AAA | GCA | ATG | CAA | GTA | GAT | ACT | ACT | CTT | GTT | GGA | TTA | TCT | CCA | CAA | 720 |
|---|---|---|---|---|---|---|---|---|---|---|---|---|---|---|---|---|
| Leu | Lys | Ala | Met | Gln | Val | Asp | Thr | Thr | Leu | Val | Gly | Leu | Ser | Pro | Gln | |
| 225 | | | | 230 | | | | | 235 | | | | | 240 | | |

| GAT | GCG | AAG | AAA | TCC | CCC | TAT | ATT | GCT | TCA | ATG | GGA | GTT | TAT | GTA | TTC | 768 |
|---|---|---|---|---|---|---|---|---|---|---|---|---|---|---|---|---|
| Asp | Ala | Lys | Lys | Ser | Pro | Tyr | Ile | Ala | Ser | Met | Gly | Val | Tyr | Val | Phe | |
| | | | | 245 | | | | | 250 | | | | | 255 | | |

| AAG | ACA | GAT | GTA | TTG | TTG | AAG | CTC | TTG | AAA | TGG | AGC | TAT | CCC | ACT | TCT | 816 |
|---|---|---|---|---|---|---|---|---|---|---|---|---|---|---|---|---|
| Lys | Thr | Asp | Val | Leu | Leu | Lys | Leu | Leu | Lys | Trp | Ser | Tyr | Pro | Thr | Ser | |
| | | | 260 | | | | | 265 | | | | | 270 | | | |

| AAT | GAT | TTT | GGC | TCT | GAA | ATT | ATA | CCA | GCA | GCT | ATT | GAC | GAT | TAC | AAT | 864 |
|---|---|---|---|---|---|---|---|---|---|---|---|---|---|---|---|---|
| Asn | Asp | Phe | Gly | Ser | Glu | Ile | Ile | Pro | Ala | Ala | Ile | Asp | Asp | Tyr | Asn | |
| | | 275 | | | | | 280 | | | | | 285 | | | | |

| GTC | CAA | GCA | TAC | ATT | TTC | AAA | GAC | TAT | TGG | GAA | GAC | ATT | GGA | ACA | ATT | 912 |
|---|---|---|---|---|---|---|---|---|---|---|---|---|---|---|---|---|
| Val | Gln | Ala | Tyr | Ile | Phe | Lys | Asp | Tyr | Trp | Glu | Asp | Ile | Gly | Thr | Ile | |
| | 290 | | | | | 295 | | | | | 300 | | | | | |

| AAA | TCG | TTT | TAT | AAT | GCT | AGC | TTG | GCA | CTC | ACA | CAA | GAG | TTT | CCA | GAG | 960 |
|---|---|---|---|---|---|---|---|---|---|---|---|---|---|---|---|---|
| Lys | Ser | Phe | Tyr | Asn | Ala | Ser | Leu | Ala | Leu | Thr | Gln | Glu | Phe | Pro | Glu | |
| 305 | | | | 310 | | | | | 315 | | | | | 320 | | |

| TTC | CAA | TTT | TAC | GAT | CCA | AAA | ACA | CCT | TTT | TAC | ACA | TCT | CCT | AGG | TTC | 1008 |
|---|---|---|---|---|---|---|---|---|---|---|---|---|---|---|---|---|
| Phe | Gln | Phe | Tyr | Asp | Pro | Lys | Thr | Pro | Phe | Tyr | Thr | Ser | Pro | Arg | Phe | |
| | | | | 325 | | | | | 330 | | | | | 335 | | |

| CTT | CCA | CCA | ACC | AAG | ATA | GAC | AAT | TGC | AAG | ATT | AAG | GAT | GCC | ATA | ATC | 1056 |
|---|---|---|---|---|---|---|---|---|---|---|---|---|---|---|---|---|
| Leu | Pro | Pro | Thr | Lys | Ile | Asp | Asn | Cys | Lys | Ile | Lys | Asp | Ala | Ile | Ile | |
| | | | 340 | | | | | 345 | | | | | 350 | | | |

| TCT | CAT | GGA | TGT | TTC | TTG | CGA | GAT | TGT | TCT | GTG | GAA | CAC | TCC | ATA | GTG | 1104 |
|---|---|---|---|---|---|---|---|---|---|---|---|---|---|---|---|---|
| Ser | His | Gly | Cys | Phe | Leu | Arg | Asp | Cys | Ser | Val | Glu | His | Ser | Ile | Val | |
| | | 355 | | | | | 360 | | | | | 365 | | | | |

| GGT | GAA | AGA | TCG | CGC | TTA | GAT | TGT | GGT | GTT | GAA | CTG | AAG | GAT | ACT | TTC | 1152 |
|---|---|---|---|---|---|---|---|---|---|---|---|---|---|---|---|---|
| Gly | Glu | Arg | Ser | Arg | Leu | Asp | Cys | Gly | Val | Glu | Leu | Lys | Asp | Thr | Phe | |
| | 370 | | | | | 375 | | | | | 380 | | | | | |

| ATG | ATG | GGA | GCA | GAC | TAC | TAC | CAA | ACA | GAA | TCT | GAG | ATT | GCC | TCC | CTG | 1200 |
|---|---|---|---|---|---|---|---|---|---|---|---|---|---|---|---|---|
| Met | Met | Gly | Ala | Asp | Tyr | Tyr | Gln | Thr | Glu | Ser | Glu | Ile | Ala | Ser | Leu | |
| 385 | | | | 390 | | | | | 395 | | | | | 400 | | |

| TTA | GCA | GAG | GGG | AAA | GTA | CCG | ATT | GGA | ATT | GGG | GAA | AAT | ACA | AAA | ATA | 1248 |
|---|---|---|---|---|---|---|---|---|---|---|---|---|---|---|---|---|
| Leu | Ala | Glu | Gly | Lys | Val | Pro | Ile | Gly | Ile | Gly | Glu | Asn | Thr | Lys | Ile | |
| | | | | 405 | | | | | 410 | | | | | 415 | | |

| AGG | AAA | TGT | ATC | ATT | GAC | AAG | AAC | GCA | AAG | ATA | GGA | AAG | AAT | GTT | TCA | 1296 |
|---|---|---|---|---|---|---|---|---|---|---|---|---|---|---|---|---|
| Arg | Lys | Cys | Ile | Ile | Asp | Lys | Asn | Ala | Lys | Ile | Gly | Lys | Asn | Val | Ser | |
| | | | 420 | | | | | 425 | | | | | 430 | | | |

| ATC | ATA | AAT | AAA | GAC | GGT | GTT | CAA | GAG | GCA | GAC | CGA | CCA | GAG | GAA | GGA | 1344 |
|---|---|---|---|---|---|---|---|---|---|---|---|---|---|---|---|---|
| Ile | Ile | Asn | Lys | Asp | Gly | Val | Gln | Glu | Ala | Asp | Arg | Pro | Glu | Glu | Gly | |
| | | 435 | | | | | 440 | | | | | 445 | | | | |

| TTC | TAC | ATA | CGA | TCA | GGG | ATA | ATC | ATT | ATA | TTA | GAG | AAA | GCC | ACA | ATT | 1392 |
|---|---|---|---|---|---|---|---|---|---|---|---|---|---|---|---|---|
| Phe | Tyr | Ile | Arg | Ser | Gly | Ile | Ile | Ile | Ile | Leu | Glu | Lys | Ala | Thr | Ile | |
| | 450 | | | | | 455 | | | | | 460 | | | | | |

| AGA | GAT | GGA | ACA | GTC | ATC | TGAACTAGGG | AAGCACCTCT | TGTTGAACTA | 1440 |
|---|---|---|---|---|---|---|---|---|---|
| Arg | Asp | Gly | Thr | Val | Ile | | | | |

Arg Asp Gly Thr Val Ile
465                  470

CTGGAGATCC AAATCTCAAC TTGAAGAAGG TCAAGGGTGA TCCTAGCACG TTCACCAGTT    1500

GACTCCCCGA AGGAAGCTT    1519

( 2 ) INFORMATION FOR SEQ ID NO:10:

( i ) SEQUENCE CHARACTERISTICS:
        ( A ) LENGTH: 470 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| | | | | | | | | | | | | | | |
|---|---|---|---|---|---|---|---|---|---|---|---|---|---|---|
| Asn | Lys | Ile | Lys | Pro | Gly | Val | Ala | Tyr | Ser | Val | Ile | Thr | Thr | Glu | Asn |
| 1 | | | | 5 | | | | | 10 | | | | | 15 | |
| Asp | Thr | Gln | Thr | Val | Phe | Val | Asp | Met | Pro | Arg | Leu | Glu | Arg | Arg | Arg |
| | | | 20 | | | | | 25 | | | | | 30 | | |
| Ala | Asn | Pro | Lys | Asp | Val | Ala | Ala | Val | Ile | Leu | Gly | Gly | Gly | Glu | Gly |
| | | 35 | | | | | 40 | | | | | 45 | | | |
| Thr | Lys | Leu | Phe | Pro | Leu | Thr | Ser | Arg | Thr | Ala | Thr | Pro | Ala | Val | Pro |
| 50 | | | | | 55 | | | | | 60 | | | | | |
| Val | Gly | Gly | Cys | Tyr | Arg | Leu | Ile | Asp | Ile | Pro | Met | Ser | Asn | Cys | Ile |
| 65 | | | | | 70 | | | | | 75 | | | | | 80 |
| Asn | Ser | Ala | Ile | Asn | Lys | Ile | Phe | Val | Leu | Thr | Gln | Tyr | Asn | Ser | Ala |
| | | | | 85 | | | | | 90 | | | | | 95 | |
| Pro | Leu | Asn | Arg | His | Ile | Ala | Arg | Thr | Tyr | Phe | Gly | Asn | Gly | Val | Ser |
| | | | 100 | | | | | 105 | | | | | 110 | | |
| Phe | Gly | Asp | Gly | Phe | Val | Glu | Val | Leu | Ala | Ala | Thr | Gln | Thr | Pro | Gly |
| | | 115 | | | | | 120 | | | | | 125 | | | |
| Glu | Ala | Gly | Lys | Lys | Trp | Phe | Gln | Gly | Thr | Ala | Asp | Ala | Val | Arg | Lys |
| | 130 | | | | | 135 | | | | | 140 | | | | |
| Phe | Ile | Trp | Val | Phe | Glu | Asp | Ala | Lys | Asn | Lys | Asn | Ile | Glu | Asn | Ile |
| 145 | | | | | 150 | | | | | 155 | | | | | 160 |
| Val | Val | Leu | Ser | Gly | Asp | His | Leu | Tyr | Arg | Met | Asp | Tyr | Met | Glu | Leu |
| | | | | 165 | | | | | 170 | | | | | 175 | |
| Val | Gln | Asn | His | Ile | Asp | Arg | Asn | Ala | Asp | Ile | Thr | Leu | Ser | Cys | Ala |
| | | | 180 | | | | | 185 | | | | | 190 | | |
| Pro | Ala | Glu | Asp | Ser | Arg | Ala | Ser | Asp | Phe | Gly | Leu | Val | Lys | Ile | Asp |
| | | 195 | | | | | 200 | | | | | 205 | | | |
| Ser | Arg | Gly | Arg | Val | Val | Gln | Phe | Ala | Glu | Lys | Pro | Lys | Gly | Phe | Asp |
| | 210 | | | | | 215 | | | | | 220 | | | | |
| Leu | Lys | Ala | Met | Gln | Val | Asp | Thr | Thr | Leu | Val | Gly | Leu | Ser | Pro | Gln |
| 225 | | | | | 230 | | | | | 235 | | | | | 240 |
| Asp | Ala | Lys | Lys | Ser | Pro | Tyr | Ile | Ala | Ser | Met | Gly | Val | Tyr | Val | Phe |
| | | | | 245 | | | | | 250 | | | | | 255 | |
| Lys | Thr | Asp | Val | Leu | Leu | Lys | Leu | Leu | Lys | Trp | Ser | Tyr | Pro | Thr | Ser |
| | | | 260 | | | | | 265 | | | | | 270 | | |
| Asn | Asp | Phe | Gly | Ser | Glu | Ile | Ile | Pro | Ala | Ala | Ile | Asp | Asp | Tyr | Asn |
| | | 275 | | | | | 280 | | | | | 285 | | | |
| Val | Gln | Ala | Tyr | Ile | Phe | Lys | Asp | Tyr | Trp | Glu | Asp | Ile | Gly | Thr | Ile |
| | 290 | | | | | 295 | | | | | 300 | | | | |
| Lys | Ser | Phe | Tyr | Asn | Ala | Ser | Leu | Ala | Leu | Thr | Gln | Glu | Phe | Pro | Glu |
| 305 | | | | | 310 | | | | | 315 | | | | | 320 |
| Phe | Gln | Phe | Tyr | Asp | Pro | Lys | Thr | Pro | Phe | Tyr | Thr | Ser | Pro | Arg | Phe |

|     |     |     |     | 325 |     |     |     |     | 330 |     |     |     |     | 335 |     |     |
| --- | --- | --- | --- | --- | --- | --- | --- | --- | --- | --- | --- | --- | --- | --- | --- | --- |
| Leu | Pro | Pro | Thr<br>340 | Lys | Ile | Asp | Asn | Cys<br>345 | Lys | Ile | Lys | Asp | Ala<br>350 | Ile | Ile |

Ser His Gly Cys Phe Leu Arg Asp Cys Ser Val Glu His Ser Ile Val
    355                 360              365

Gly Glu Arg Ser Arg Leu Asp Cys Gly Val Glu Leu Lys Asp Thr Phe
370                    375             380

Met Met Gly Ala Asp Tyr Tyr Gln Thr Glu Ser Glu Ile Ala Ser Leu
385             390              395                    400

Leu Ala Glu Gly Lys Val Pro Ile Gly Ile Gly Glu Asn Thr Lys Ile
             405              410                 415

Arg Lys Cys Ile Ile Asp Lys Asn Ala Lys Ile Gly Lys Asn Val Ser
            420              425             430

Ile Ile Asn Lys Asp Gly Val Gln Glu Ala Asp Arg Pro Glu Glu Gly
        435              440              445

Phe Tyr Ile Arg Ser Gly Ile Ile Ile Ile Leu Glu Lys Ala Thr Ile
    450             455              460

Arg Asp Gly Thr Val Ile
465             470

( 2 ) INFORMATION FOR SEQ ID NO:11:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

GTTGATAACA AGATCTGTTA ACCATGGCGG CTTCC                    35

( 2 ) INFORMATION FOR SEQ ID NO:12:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

CCAGTTAAAA CGGAGCTCAT CAGATGATGA TTC                      33

( 2 ) INFORMATION FOR SEQ ID NO:13:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

GTGTGAGAAC ATAAATCTTG GATATGTTAC                            30

( 2 ) INFORMATION FOR SEQ ID NO:14:

( i ) SEQUENCE CHARACTERISTICS:
        ( A ) LENGTH: 28 base pairs
        ( B ) TYPE: nucleic acid ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

GAATTCACAG GGCCATGGCT CTAGACCC                    28

( 2 ) INFORMATION FOR SEQ ID NO:15:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

AAGATCAAAC CTGCCATGGC TTACTCTGTG ATCACTACTG        40

( 2 ) INFORMATION FOR SEQ ID NO:16:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

GGGAATTCAA GCTTGGATCC CGGGCCCCCC CCCCCCCC          39

( 2 ) INFORMATION FOR SEQ ID NO:17:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

GGGAATTCAA GCTTGGATCC CGGG                         24

( 2 ) INFORMATION FOR SEQ ID NO:18:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

CCTCTAGACA GTCGATCAGG AGCAGATGTA CG                32

( 2 ) INFORMATION FOR SEQ ID NO:19:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

GGAGTTAGCC ATGGTTAGTT TAGAG                                                                25

( 2 ) INFORMATION FOR SEQ ID NO:20:

( i ) SEQUENCE CHARACTERISTICS:
    ( A ) LENGTH: 34 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:20:

GGCCGAGCTC GTCAACGCCG TCTGCGATTT GTGC                                                      34

( 2 ) INFORMATION FOR SEQ ID NO:21:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:21:

GATTTAGGTG ACACTATAG                                                                       19

( 2 ) INFORMATION FOR SEQ ID NO:22:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:22:

AGAGAGATCT AGAACAATGG CTTCCTCTAT GCTCTCTTCC GC                                              42

( 2 ) INFORMATION FOR SEQ ID NO:23:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:23:

GGCCGAGCTC TAGATTATCG CTCCTGTTTA TGCCCTAAC                                                  39

( 2 ) INFORMATION FOR SEQ ID NO:24:

( i ) SEQUENCE CHARACTERISTICS:
    ( A ) LENGTH: 2196 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:24:

ATCGATTATT GGTTTATCGG GTTTTGATCG TTATCGGTTC GGTTTAACCG TTAAAATTTG            60

ACACAAAAAT AAAAATTGAA AAGCACTTAG AAACAAGGTG ACAAACCTAA TAAACCATGC          120

-continued

```
ACATGAGTTC ACAAGTTACA TCTTGCTAAA AAACAAACAC TTTTACATTG TAGAATAACC    180
AAGTGTCTGG GACAACCAAA AATGAAAGTA GGAAACCAAA CTCTAAGTCA AGGACTTTAT    240
ATACAAAATG GTATAACTAT AATTATTTAA TTTACTATTG GGTTATCGGT TAACCCGTTA    300
AGAACCGATA ACCCGATAAC AAAAACAATC AAAATCGTTA TCAAAACCGC TAAACTAATA    360
ACCCAATACT GATAAACCAA TAACTTTTTT TTTATTCGGG TTATCGGTTT CAGTTCGGTT    420
TTGAACAATC CTAGTGTCCT AATTATTGTT TTGAGAACCA AGAAAACAAA AACTGACGTC    480
GCAAATATTT CAGTAAATAC TTGTATATCT CAGTGATAAT TGATTCCAA DATGTATAAT    540
TATCATTTAC GTAATAATAG ATGGTTTCCG AAACTTACGC TTCCCTTTTT TCTTTTGCAG    600
TCGTATGGAA TAAAGTTGGA TATGGAGGCA TTCCCGGGCC TTCAGGTGGA AGAGACGGAG    660
CTGCTTCACA AGGAGGGGGT TGTTGTACTT GAAAATAGGC ATTTATTCCG TTCGCAAACC    720
TATCATGTTC CTATGGTTGT TTATTTGTAG TTTGGTGTTC TTAATATCGA GTGTTCTTTA    780
GTTTGTTCCT TTTAATGAAA GGATAATATC TCGTGCCAAA AATAAGCAAA TTCGGTACAT    840
AAAGACATTT TTTTTCTTTC GTGGATTTTC TGTTTATGGA GTTGTCAAAT GTGGAATTTA    900
TTTCATAGCA TGTGGAGTTT CCTCCTCTCC TTTTTCATGT GCCCTTGGGC CTTGCCTGTT    960
TCTTGCACCG CAGTGTGCCA GGGCAGTCGG CAGATGGACA TAAATGGCAC ACCGCTCGGC   1020
TCGTGGAAAG AGTATGGTCA GTTTCATTGA TAAGTATTTA CTCGTATTCG GCGTATACAT   1080
CAAGTTAATA GAAAGTAAAC ACATATGATA TCATACATCC ATTAGTTAAG TATAAATGCC   1140
AACTTTTTAC TTGAATCGCT GAATAAATTT ACTTACGATT AATATTTAGT TGTGTGTTCA   1200
AACATATCAT GCATTATTTG ATTAAGAATA AATAAACGAT GTGTAATTTG AAAACCAATT   1260
AGAAAAGAAG TATGACGGGA TTGATGTTCT GTGAAATCAC TGGCAAATTG AACGGACGAT   1320
GAAATTTGAT CGTCATTTAA ACATATCAAC ATGGCTTTAG TCATCATCAT TATGTTATAA   1380
TTATTTTCTT GAAACTTGAT ACACCAACTC TCATTGGGAA AGTGACAGCA TAATATAAAC   1440
TATAATATCA ATCTGGCAAT TTCGAATTAT TCCAAATCTC TTTTGTCATT TCATTTCATC   1500
CCCTATGTCT GCCTGCAAGT ACCAATTATT TAAATACAAA AATCTTGATT AAACAATTCA   1560
TTTTCTCACT AATAATCACA TTTAATAATA AACGGTCAT ACACGTGCGT CACCTTTTTT   1620
TCGATTTTCT CTCAAGCGCA TGTGATCATA TCTAACTCTT GTGCAAACAA GTGAAATGAC   1680
GTCCATTAAT AAATAATCTT TTGAATACCT GTTCATTTA ATTTATTTGG ATTTGCTAAG   1740
GATTTTTTTT AGTTTTGAG ATTTTTATA ATTTAAATT AAAAAAAATA AGTTAAATAT   1800
ATCGAAAATG TCTTTAATC TTATTTTTGA AAAAGATAAT TAGCTCAAAC AAATTAAAAT   1860
TGGTAACTAT TTTTCGGAAA AATAATGATT CTTATTGTAC ATTCTTTTTC ATCGATTAGA   1920
TATTTTTTTT AAGCTCAAGT ACAAAAGTCA TATTTCAATC CCCAAAATAG CCTCAATCAC   1980
AAGAAATGCT TAAATCCCCA AAATACCCTC AATCACAAAA AGTGTACCAA TCATAACTAT   2040
GGTCCTCTGT AAATTCCAAC AAAATCAAGT CTATAAAGTT ACCCTTGATA TCAGTACTAT   2100
AAAACCAAAA ATCTCAGCTG TAATTCAAGT GCAATCACAC TCTACCACAC ACTCTCTAGT   2160
AGAGAAATCA GTTGATAACA AGCTTTGTTA ACAATG                              2196
```

( 2 ) INFORMATION FOR SEQ ID NO:25:

( i ) SEQUENCE CHARACTERISTICS:
        ( A ) LENGTH: 591 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:25:

| | | | | | | |
|---|---|---|---|---|---|---|
| AAGCTTGATA | TCGAATTCCT | GCAGCCCGGG | GGATCTCCTT | AAAACTTTTT | CTGAATTACT | 60 |
| TTTCAAGATT | CTTGATTCTG | CACCACTAGC | AATTTCCATT | TTTCTTTCAG | TGATTTTGGT | 120 |
| TACTTATTTG | ACATTCTTGT | TTTCAAGATC | CAACATCATC | ACTTCCAGG | TTCAAAATCT | 180 |
| TGTTTTTTTT | CTTTTTTCTT | TTAATGCTCT | ATATTGTGGA | AGTCCACAGG | TGAATTTTA | 240 |
| CGATATGGGT | TTACCACTTA | GCTTCTTGT | AATATTTAT | CAATTTAGA | AAATATATGT | 300 |
| GTGAAATACC | TAATTTTACG | TAGAGATCAT | GGGTTCATAT | GCGTAAAGAT | TCATGTTTTT | 360 |
| GTGGTAATGC | TATGAGGTAT | TAGTACTGAG | CATATAGCTA | GCTTGGGTTT | TGGGTTTACC | 420 |
| GACCAAAAAA | AAAAATTAGT | GATATTTCT | TTATGTAAAT | TATACTTTTC | TTGGTTGCTA | 480 |
| AAAGATAACA | TATACTTTAT | TGAGATTTGA | ATAAATCTAT | TTGATTAGA | TCCATTGATA | 540 |
| AATCTTAATC | TTATGGGATT | ACTGATTTGT | TGATTGGCTG | CAGAAGGATC | C | 591 |

( 2 ) INFORMATION FOR SEQ ID NO:26:

( i ) SEQUENCE CHARACTERISTICS:
        ( A ) LENGTH: 1705 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:26:

| | | | | | | |
|---|---|---|---|---|---|---|
| AAGCTTGGGT | ACCGGGCCCC | CCCTGGAGGT | CGAGTGCCAT | CACATCCAGG | GTGTAGGCTC | 60 |
| GGGGCGTGAC | AAACTTGGTA | TCTGAGCTCA | GAGTTCAAGA | GTCTAAGGTG | TCTATAAAGT | 120 |
| CTGTGCCTTT | AGAGTCCTAG | TTATCGGTGT | GAAGCGCGCC | ACATCTATAA | CCAGGAGGCT | 180 |
| GCGACATTTA | AGAATTATCA | TACTTCTTTC | ATACTCTTTT | CGTGCAATAG | AGTTCAACTC | 240 |
| CATAAAGTCT | CTTTATAATT | CATGTTTACG | CATATCTTTG | AGATCATGCC | TCCATGTAGA | 300 |
| GTTGTCTGAG | GTCGTCCTGC | TAGAAGAAAT | ATTGATCCTC | AGGATCAAGG | GGTACCCAAT | 360 |
| GCACCAGAAG | TGCGACCCCA | AGGAAAGGTC | ACTAATGTTG | AGTTCCAGGA | TGTTATACGG | 420 |
| ATATTGAGTG | AAGTTGTGAC | CAACCAAGCT | GGACAACAAA | GAGGGAATCA | ACAAGATGTG | 480 |
| GTTGATACAT | CCAGAATCCG | TGAGTTCTTA | AGGATGAATC | CTTCAGACTT | CACCAATTCA | 540 |
| AGAGTCACTG | AGGATCTGGA | AAACTTTGTG | GAAGAGTTGT | AGAAGGTTTT | TGAGGTTATG | 600 |
| CATGTTGTTG | ATGCTGAGCG | AGTGGAACTA | ACTGCATACC | AACTGAATGG | TGTTGCTAGA | 660 |
| GTATGGTACG | ACCAATAGAA | AAAGAGTAGA | GTTGAGGGTG | CACAAATTGT | GAGTTGGGCA | 720 |
| GTGTTTGAAG | AGGCCTTCAT | GGGGCATTTC | TTTTCCCATG | AACTATATGG | CAAAGGTAAG | 780 |
| AGAATTTCCT | CACTCTTAAG | CAGGAATCCA | TGAGTGTGCA | TAAGTATAGC | CTCAAGTTCA | 840 |
| CTCAACTGTC | GCCTATGCTC | CAGAGATGGC | TGTTGATATG | AGGAGCAGGA | TGGGCTTGTT | 900 |
| TGTGTTTGGG | TTGTCTCATC | TGTCAATCAA | AGAAGGTAAG | GTTGTGATGT | GGATAAAGGA | 960 |
| CATGGACATC | GAAAGGGTAA | TGATCCTTGT | GCAACAGGTT | GAGGAAGATA | AGTTGAGGGA | 1020 |
| TAGAGAAGAG | TTCTGAAACA | AGAGGGCTAA | GAACACATGA | AATGAGTACG | TAAGCAGAAG | 1080 |
| AGTAATGCAA | ATCGGTTATC | TTTTCAATGA | AAGCCAAATA | AACCTGCTTG | ATTGTTTGCA | 1140 |
| AGTGCAACCT | GTACCAACGA | ACAAAGGTGA | GTTCAAGAAT | CAGAATTCTT | AGAAATTCAG | 1200 |
| AGCTAGACCT | GCACAATCTC | AAGGTAGTGT | GGCACAAGGA | TGTAATGGGA | CTCCTGCATG | 1260 |
| TGTTAAGTAC | GGTAGGAACC | ACCCAGGAGC | GTGTCATGAT | GGCTCTGCTG | GTTGCTTCAA | 1320 |

-continued

| | | | | | | |
|---|---|---|---|---|---|---|
| GTGTGGTCAG | AATGGTCACT | TCATGAGAGA | GTGCCTAAAG | AANAGGCAAG | GTAATAGCAA | 1380 |
| TGGGGGCAAT | ATATCACAAT | CTTCTTCAGT | GGCTCCACNA | GATAGAGCTG | CACCTTGAGG | 1440 |
| ATCATGGGTT | CATATGCGTA | AAGATTCATG | TTTTGTGGTA | ATGCTATGAG | GTATTAGTAC | 1500 |
| TGAGCATATA | GCTAGCTTGG | GTTTGGGTT | TACCGACCAT | TTTTTTAAT | TAGTGATATT | 1560 |
| TTCTTTATGT | ATTTATACT | TTTCTTGGTT | GCTTAAAGAT | TACATATACT | TTATTGAGAT | 1620 |
| TTGAATAAAT | CTATTTGATT | TAGATCCATT | GATAAATCTT | AATCTTATGG | GATTACTGAT | 1680 |
| TTGTTGATTG | GCTGCAGAAG | GATCC | | | | 1705 |

METHOD OF IMPROVING THE QUALITY OF STORED POTATOES

This application is a continuation-in-part of Ser. No. 070,155, filed May 28, 1993, now abandoned.

BACKGROUND OF THE INVENTION

Long term storage properties of potato represents a major determinant of tuber quality. Dormancy periods (the time period after harvesting and before sprouting) are crucial to maintaining quality potatoes. Commercially, potatoes may be held for long periods before processing (up to 10 months or longer), and at temperatures typically between 2°–10° C. Cold storage (2°–6° C.) versus storage at 7°–12° C. provides the best long term conditions by reducing respiration, water loss, microbial infection, and the need for chemical sprout inhibitors (Burton, 1989). However, low temperatures lead to cold-induced sweetening, and the resultant high sugar levels contribute to an unacceptable brown color in the fried product (Coffin et al., 1987, Weaver et al., 1978). The sugars that accumulate are predominantly glucose, fructose, and sucrose, and it is mainly the reducing sugars (primarily glucose and fructose) which react with free amino groups upon heating during the various cooking processes, including frying, via the Maillard reaction, and result in the formation of brown pigment (Burton, 1989, Shallenberger et al., 1959). Sucrose, on the other hand, produces a black coloration on frying due to its susceptibility to undergo carmelization as well as charring. Levels of reducing sugars above 0.2% fresh weight are sufficient to cause brown pigment formation and thus merit rejection for certain types of processing. A potato processor can reduce the levels of sugars by a costly and time consuming blanching process if the levels of sugars are not significantly higher than the 0.2% limit. Potatoes can be reconditioned at higher temperatures (18° C.) to lower sugar content, but often sugar levels will not sufficiently decrease before the onset of sprouting at these temperatures, requiring the use of chemical sprout inhibitors (Ryall and Lipton, 1979, Hardenburg et al., 1986). However, reconditioning increases the storage facility requirements and consequently affects the final cost of the product. Furthermore, it has been shown that reconditioning is not effective after longer storage periods (Coffin et al., 1987). Given the negative environmental and health perceptions associated with excessive chemical use, and the fact that current sprout inhibitors may soon be banned, a need exists for potato varieties which can withstand long term cold storage without the use of chemicals, without accumulation of reducing sugars, and with greater retention of starch levels.

After longer storage periods, sprouting of potato tubers becomes a problem. Excess sprouting reduces the market value and can cause increased levels of alkaloids in the tuber.

Through the process of genetic engineering potato tubers which contain significantly higher levels of starch have been obtained. See WO 91/19806 (Kishore), also U.S. Ser. No. 07/709,663, filed Jun. 7, 1991, now abandoned, hereby incorporated by reference. In these tubers a gene is expressed which encodes ADPglucose pyrophosphorylase (ADPGPP), which catalyzes a key step in starch and glycogen biosynthesis. The preferred gene is from *E. coli* and the resulting enzyme is a poorly regulated, highly active variant. When a mutant of this gene, glgC16, is expressed in a tuber-specific manner, for example from a class I patatin promoter, starch levels are higher than those of nontransgenic control tubers at the time of harvest.

Carbohydrate metabolism is a complex process in plant cells. Manipulation of a number of different enzymatic processes potentially may effect the accumulation of reducing sugars during cold storage. For example, sugars may be used to resynthesize starch, and thus effect reduction in the pool of free sugar. Other methods may also serve to enhance the cold storage properties of potato through reduction of sugar content, including the inhibition of starch hydrolysis, removal of sugars through glycolysis, or conversion of sugars into other forths which would not participate in the Maillard reaction. The challenge in these methods would be to identify an activity with which to effect the desired result, achieve function at low temperatures, and still retain the product qualities desired by potato growers, processors, and consumers.

It has been suggested that phosphofructokinase (PFK) plays an important role in the cold-induced sweetening process (Kruger and Hammond, 1988, ap Rees et al., 1988, Dixon et al., 1981, Claassen et al., 1991). ap Rees et al. (1988) suggested that cold treatment had a disproportionate effect on different pathways in carbohydrate metabolism in that glycolysis was more severely reduced due to the cold-lability of PFK. The reduction in PFK activity would then lead to an increased availability of hexose-phosphates for sucrose production. Additional support for this view comes from the observation of a new breeding clone of potato which contains a PFK which is not cold labile and that does not accumulate significant amounts of sugar in the cold.

It was recently disclosed in European Patent Application 0 438 904 that increasing PFK activity reduces sugar accumulation during storage by removing hexoses through glycolysis and further metabolism. A PFK enzyme from *E. coli* was expressed in potato tubers and the report claimed to increase PFK activity and to reduce sucrose content in tubers assayed at harvest. However, it has been shown that pyrophosphate:Fructose 6-phosphate phosphotransferase (PFP) remains active at low temperatures (Claassen et al., 1991). PFP activity can supply fructose 6-phosphate for glycolysis just as PFK can since the two enzymes catalyze the same reaction. Therefore the efficacy of this approach in improving the cold storage quality of potato tubers remains in doubt. Furthermore, the removal of sugars through glycolysis and further metabolism would not be a preferred method of enhancing storage properties of potato tubers because of the resultant loss of valuable dry matter content through respiration. Resynthesis of the sugars into starch or slowing the breakdown of starch would be preferred because dry matter would be retained.

It is an object of this invention to provide a method for reducing the level of sugars within potato tubers and to provide improved quality of stored potatoes. It is a further object of this invention to provide potatoes having an improved rate and degree of reconditioning after storage at reduced temperatures. It is a still further object of this invention to provide a method of extending dormancy of potatoes stored at ambient temperatures or at reduced temperatures.

SUMMARY OF THE INVENTION

The present invention provides a method of improving the quality of potatoes stored at low temperatures comprising providing an increased level of ADPglucose pyrophosphorylase (ADPGPP) enzyme activity within the potato tuber during storage at reduced temperatures. Also provided is a method of reducing the level of sugars within potato tubers stored at reduced temperatures by increasing the ADPGPP enzyme activity during cold storage. Further provided is a method of prolonging dormancy of stored potatoes comprising increasing the ADPGPP enzyme activity during storage.

This method is preferably accomplished by:

(a) inserting into the genome of a potato plant cell a recombinant, double-stranded DNA molecule comprising (i) a promoter which functions in plants to cause the production of an RNA sequence in target plant tissues, (ii) a structural DNA sequence that causes the production of an RNA sequence which encodes a fusion polypeptide comprising an amino-terminal plastid transit peptide and an ADPglucose pyrophosphorylase enzyme, (iii) a 3' nontranslated DNA sequence which functions in plant cells to cause transcriptional termination and the addition of polyadenylated nucleotides to the 3' end of the RNA sequence;

(b) obtaining transformed plant cells; and (c) regenerating from the transformed plant cells genetically transformed potato plants which have improved cold storage properties.

Novel recombinant DNA molecules, plant cells, and regenerated potato plants are provided wherein the promoter of (a)(i) is a cold-inducible promoter, such as from potato or Arabidopsis. These regenerated potato plants are useful in all of the methods of the present invention.

A preferred ADPglucose pyrophosphorylase (ADPGPP) enzyme is that from E. coli, known as glgC, which gene sequence is shown below as SEQ ID NO:1 and which amino acid sequence is shown as SEQ ID NO:2. A more preferred ADPGPP enzyme is the mutant ADPGPP, glgC16, which gene sequence is shown below as SEQ ID NO:3 and which amino acid sequence is shown below as SEQ ID NO:4. This mutant has been found to have a higher affinity to substrates in the absence of the activator, fructose 1,6-bisphosphate (FBP), and to reach half-maximal activation with a decreased concentration of FBP.

As used herein, the term "improving the quality of stored potatoes," or variants thereof, shall mean providing potatoes which after storage have reduced levels of sugars, little or no loss of starch, reduced incidence of sprouting, and/or an enhanced rate or degree of reconditioning.

As used herein, the term "cold storage" or "storage at reduced temperature," or variants thereof, shall mean holding at temperatures less than or equal to 15° C., which may be caused by refrigeration or ambient temperatures.

As used herein, the term "cold-inducible promoter" shall mean a sequence of DNA bases that initiates the transcription of mRNA using one of the DNA strands as a template to make a corresponding complimentary strand of RNA when the temperature is equal to or less than 15° C.

As used herein, the term "prolonging dormancy" or variants thereof shall mean delaying onset of respiration and sprouting of tubers.

As used herein, the term "glgC16 potatoes," "glgC16 tubers," "glgC16 lines," or variants thereof, shall mean potato lines or tubers therefrom which have been transformed with a fusion of a plastid terminal transit peptide, preferably CTP, described below.

DETAILED DESCRIPTION OF THE INVENTION

Figure 1:
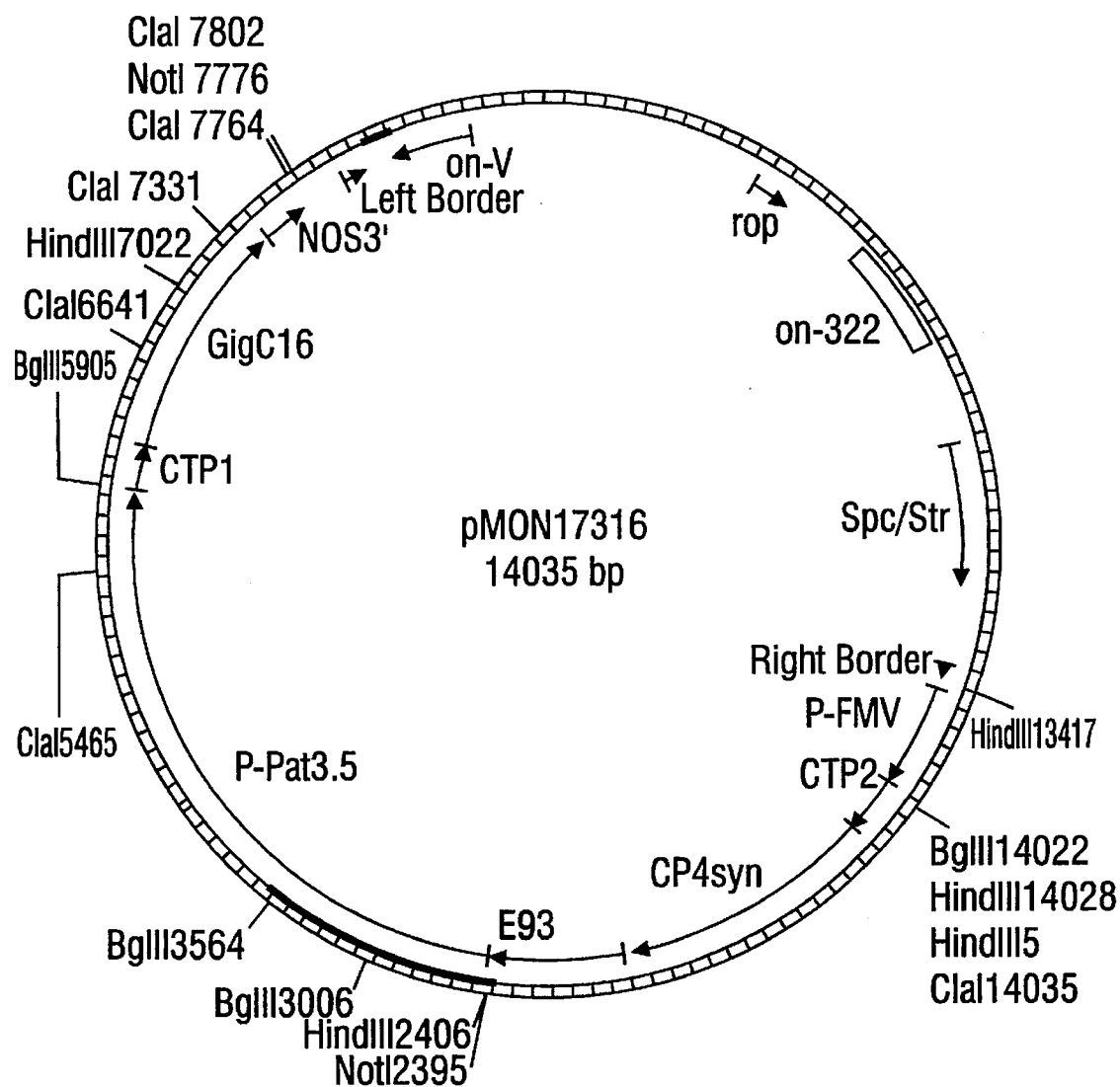
FIG. 1 shows a plasmid map for plant transformation vector pMON17316.

Starch phosphorylase and amylolytic enzymes are responsible for starch degradation during cold storage and result in the formation of glucose 1-phosphate and/or glucose from starch. Glucose may be convened to glucose 1-phosphate and serve as a substrate for the ADPGPP enzyme and thus for starch biosynthesis in the tubers expressing this enzyme. Glucose 1-phosphate may also be formed from the products of degradation of sucrose via invertase or sucrose synthase. Reducing sugars primarily accumulate during storage rather than sucrose due to the action of invertase (Pressey, 1966). The glucose and fructose released from invertase activity can also serve as precursors of substrates for starch biosynthesis.

The expression of ADPGPP is an effective means of countering the effects of cold-induced sweetening. It is hypothesized that by maintaining starch biosynthesis during cold storage, the continuous demand on the hexose pool is such that sugar accumulation is reduced and thus the tuber remains suitable for processing. However, other mechanisms may also be responsible for this effect of ADPGPP. In addition, prolonging the dormancy of potatoes stored at any temperature may also be accomplished by keeping the sugar level low and delaying onset of respiration and thus sprouting.

In order to accomplish the foregoing, a gene for expression of ADPGPP is incorporated within the genome of potato plants. This gene may be combined with other genes (in sense or antisense orientation) for regulation of starch and/or sugar metabolism/catabolism in potatoes, for example, phosphofrutcokinases (EP 0 438 904); α- and β-amylases; sucrose phosphate synthases; hexokinases; starch phosphorylases; debranching enzymes; or phosphoglucomutases. These additional genes may be from a plant, microorganism, or animal source.

Alternatively, increased levels of ADPGPP in stored tubers may be achieved by mutagenizing potato clones and thus increasing ADPGPP enzyme activity levels. Such tubers could be selected based on display of increased specific activity, increased $V_{max}$, reduced inhibition by the negative effector ($P_i$), or reduced dependence upon activator (3-PGA) for maximal activity.

The expression of a plant gene which exists in double-stranded DNA form involves transcription of messenger RNA (mRNA) from one strand of the DNA by RNA polymerase enzyme, and the subsequent processing of the mRNA primary transcript inside the nucleus. This processing involves a 3' nontranslated region which adds polyadenylate nucleotides to the 3' end of the RNA.

Transcription of DNA into mRNA is regulated by a region of DNA usually referred to as the "promoter." The promoter region contains a sequence of bases that signals RNA polymerase to associate with the DNA, and to initiate the transcription of mRNA using one of the DNA strands as a template to make a corresponding complimentary strand of RNA.

A number of promoters which are active in plant cells have been described in the literature. These include the nopaline synthase (NOS) and octopine synthase (OCS) promoters (which are carried on tumor-inducing plasmids of Agrobacterium tumefaciens), the caulimovirus promoters such as the cauliflower mosaic virus (CaMV) 19S and 35S and the figwort mosaic virus 35S-promoters, the light-inducible promoter from the small subunit of ribulose-1,5-bis-phosphate carboxylase (ssRUBISCO, a very abundant plant polypeptide), and the chlorophyll a/b binding protein gene promoter, etc. All of these promoters have been used to create various types of DNA constructs which have been expressed in plants; see, e.g., PCT publication WO 84/02913.

The class I patatin promoters used in Examples 1 and 2 below, have been shown to be both highly active and tuber-specific (Bevan et al., 1986; Jefferson et al., 1990). A number of other genes with tuber-specific or enhanced expression are known, including the potato tuber ADPGPP genes, large and small subunits (Muller et al., 1990), sucrose synthase (Salanoubat and Belliard, 1987, 1989), the major tuber proteins including the 22 kd protein complexes and proteinase inhibitors (Hannapel, 1990), the granule bound starch synthase gene (GBSS) (Rohde et al., 1990), and the other class I and II patatins (Rocha-Sosa et al., 1989; Mignery et al., 1988). Other promoters which are contemplated to be useful in this invention include those that show enhanced or specific expression in potato tubers, that are promoters normally associated with the expression of starch biosynthetic or modification enzyme genes, or that show different patterns of expression within the potato tuber, with cortex-or pith- or periderm-enhanced expression, for example, or are expressed at different times during tuber development. Examples of these promoters include those for the genes for the granule-bound and other starch synthases, the branching enzymes (Kossmann et al., 1991; Bleunow, A. and Johansson, G., 1991; WO 92/14827; WO 92/11375), disproportionating enzyme (Takaha et al., 1993), debranching enzymes, amylases, starch phosphorylases (Nakano et al., 1989; Mori et al., 1991), pectin esterases (Ebbelaar, et al., 1993), the 40 kD glycoprotein; ubiquitin, aspartic proteinase inhibitor (Stukerlj et al., 1990), the carboxypeptidase inhibitor, tuber polyphenol oxidases (Shahar et al., 1992; GenBank® Accession Numbers M95196 and M95197), putative trypsin inhibitor and other tuber cDNAs (Stiekema et al., 1988), and for β-amylase and sporarnins (from *Ipomoea batatas*; Yoshida et al., 1992; Ohta et al., 1991).

Expression of bacterial ADPGPP from various potato promoters has been shown by Kishore in PCT Application WO 91/19806 to result in an increase in starch content in potato tubers.

It is not a requirement of the present method to start with a tuber with high starch content to achieve low reducing sugar accumulation during cold storage. The glgC16 gene can be expressed from a cold-induced promoter in potato so that the GlgC16 enzyme is only present during storage conditions. The presence of this enzyme would then maintain starch biosynthesis during storage and thus prevent the accumulation of sugars.

Examples of cold-inducible promoters, including plant promoters are numerous (Yamaguchi-Shinozaki et al., 1993; Qoronfleh et al., 1992; Miner et al., 1992; Houde et al., 1992; White et al., 1992; Huang et al., 1987; Murata et al., 1992; Gilmour et al., 1992, Hajela et al., 1990; and Kurkela et al., 1990). Isolation of cold-induced proteins in potato tubers has been demonstrated (van Berkel et al., 1991, van Berkel et al., 1994). The promoters driving cold-induced expression of these proteins can be isolated by methods available to those skilled in the art. One method involves production of a cDNA library from cold stressed tubers and subsequent identification of cold-specific clones by differential hybridization with a non-stressed library. This process can be made more efficient by using subtraction libraries wherein clones expressed in a non-cold-specific manner are removed from the library during construction. The determination of the nucleotide sequences of cDNA's derived from these regulated transcripts will also facilitate the isolation of the corresponding promoter regions. The sequences of such cDNAs are know for a number of the potato tuber cold regulated transcripts (van Berkel et al., 1994). The promoter fragment could then be identified from a genomic clone using cDNA probes identified as cold-specific. Such cold regulated promoters have been identified and sequenced (Yamaguchi-Shinozaki and Shinozaki, 1994, and Baker, 1994). The promoter fragment can be used to direct expression of the *E. coli* glgC16 gene in a cold-induced manner. Additionally, one of several other ADPGPP enzymes could be expressed from this promoter to affect sugar concentration in cold stored potato tubers and thus improve the quality of the tubers. Hybrid promoters or fusions of regulatory elements of different promoters may also be employed to increase the expression level of a cold regulated promoter or to make such expression more specific to the desired plant organ. Cold regulated genes have been described in which the expression is preferential in different tissues (Zhu et at., 1993) or in which the genes are regulated more specifically by cold than by other stress effects (Wilhelm and Thomashow, 1993; Nordin et al., 1993). In addition, specific defined sequences, of sizes from 9 base pairs to a few hundred base pairs in length, have been shown to control the reponsiveness of the promoters to different cold and to other stress effects such as abscisic acid levels and to drought stress (Yamaguchi-Shinozaki and Shinozaki, 1994 ). Promoters that express preferentially in tubers are know and the regions of these promoters that are necessary for this preferential expression have also been determined (Jefferson et al., 1990; Liu et al., 1990). These data enable the construction of fusions between the small cold responsive element from promoters such as those from cor78, cor 15a, or cor15b, for example, and a patatin promoter. Fusions are made to the −500 to −2000 bp region of the patatin promoter. Current molecular genetic techniques, including Polymerase Chain Reaction and site-directed mutagenesis, and the facility of oligonucleotide synthesis make these fusions possible.

The amino-terminal plastid transit peptide used with the ADPGPP gene is needed to transport the enzyme to the plastid where starch synthesis occurs. Alternatively, the transit peptide could be omitted and the gene could be inserted into the DNA present in the plastid. Chloroplast transformation may be accomplished using the methods described by Svab et .al., 1990.

Production of Altered ADPglucose
Pyrophosphorylase Genes by Mutagenesis

Those skilled in the art will recognize that while not absolutely required, enhanced results are to be obtained by using ADPglucose pyrophosphorylase genes which are subject to reduced allosteric regulation ("deregulated") and more preferably not subject to significant levels of allosteric regulation ("unregulated") while maintaining adequate catalytic activity. The structural coding sequence for a bacterial or plant ADPglucose pyrophosphorylase enzyme can be mutagenized in *E. coli* or another suitable host and screened for increased glycogen production as described for the glgC16 gene or *E. coli*. It should be realized that use of a gene encoding an ADPglucose pyrophosphorylase enzyme which is only subject to modulators (activators/inhibitors) which are present in the selected plant at levels which do not significantly inhibit the catalytic activity will not require enzyme (gene) modification. These "unregulated" or "deregulated" ADPglucose pyrophosphorylase genes can then be inserted into plants as described herein to obtain transgenic plants having increased starch content.

For example, any ADPglucose pyrophosphorylase gene can be cloned into the E. coli B strain AC70R1-504 (Leung, 1986). This strain has a defective ADPglucose pyrophosphorylase gene, and is depressed five- to seven-fold for the other glycogen biosynthetic enzymes. The ADPglucose pyrophosphorylase gene/cDNA's can be put on a plasmid behind the E. coli glgC promoter or any other bacterial promoter. This construct can then be subjected to either site-directed or random mutagenesis. After mutagenesis, the cells would be plated on rich medium with 1% glucose. After the colonies have developed, the plates would be flooded with iodine solution (0.2 w/v % $I_2$, 0.4 w/v % KI in $H_2O$, Creuzet-Sigal, 1972). By comparison with an identical plate containing non-mutated E. coli, colonies that are producing more glycogen can be detected by their darker staining.

Since the mutagenesis procedure could have created promoter mutations, any putative ADPglucose pyrophosphorylase mutant from the first round screening will have to have the ADPglucose pyrophosphorylase gene recloned into non-mutated vector and the resulting plasmid will be screened in the same manner. The mutants that make it though both rounds of screening will then have their ADPglucose pyrophosphorylase activities assayed with and without the activators and inhibitors. By comparing the mutated ADPglucose pyrophosphorylase's responses to activators and inhibitors to the non-mutated enzymes, the new mutant can be characterized.

The report by Plaxton and Preiss in 1987 demonstrates that the maize endosperm ADPglucose pyrophosphorylase has regulatory properties similar to those of the other plant ADPglucose pyrophosphorylases (Plaxton and Preiss 1987). They show that earlier reports claiming that the maize endosperm ADPglucose pyrophosphorylase had enhanced activity in the absence of activator (3-PGA) and decreased sensitivity to the inhibitor ($P_i$), was due to proteolytic cleavage of the enzyme during the isolation procedure. By altering an ADPglucose pyrophosphorylase gene to produce an enzyme analogous to the proteolytically cleaved maize endosperm ADPglucose pyrophosphorylase, decreased allosteric regulation will be achieved.

To assay a liquid culture of E. coli for ADPglucose pyrophosphorylase activity, the cells are spun down in a centrifuge and resuspended in about 2 ml of extraction buffer (0.05M glycylglycine pH 7.0, 5.0 mM DTE, 1.0 mM EDTA) per gram of cell paste. The cells are lysed by passing twice through a French Press. The cell extracts are spun in a microcentrifuge for 5 minutes, and the supernatants are desalted by passing through a G-50 spin column.

The enzyme assay for the synthesis of ADPglucose is a modification of a published procedure (Haugen et al., 1976). Each 100 µl assay contains: 10 µmole Hepes pH 7.7, 50 µg BSA, 0.05 µmole of [$^{14}C$]glucose-1-phosphate, 0.15 µmole ATP, 0.5 µmole $MgCl_2$, 0.1 µg of crystalline yeast inorganic pyrophosphatase, 1 mM ammonium molybdate, enzyme, activators or inhibitors as desired, and water. The reaction mixture is incubated at 37° C. for 10 minutes, and is stopped by boiling for 60 seconds. The assay is spun down in a microcentrifuge, and 40 µl of the supernatant is injected onto a Synchrom Synchropak AX-100 anion exchange HPLC column. The sample is eluted with 65 mM KPi pH 5.5. Unreacted [$^{14}C$]glucose-1-phosphate elutes around 7–8 minutes, and [$^{14}C$]ADPglucose elutes at approximately 13 minutes. Enzyme activity is determined by the amount of radioactivity found in the ADPglucose peak.

The plant ADPGPP enzyme activity is tightly regulated, by both positive (3-phosphoglycerate; 3-PGA) and negative effectors (inorganic phosphate; $P_i$) (Ghosh and Preiss, 1966; Copeland and Preiss 1981; Sowokinos and Preiss 1982; Morell et al., 1987; Plaxton and Preiss, 1987; Preiss; 1988;) and the ratio of 3-PGA:$P_i$ plays a prominent role in regulating starch biosynthesis by modulating the ADPGPP activity (Santarius and Heber, 1965; Heldt et al., 1977; Kaiser and Bassham, 1979). The plant ADPGPP enzymes are heterotetramers of two large/"shrunken" and two small/"Brittle" subunits (Morell et al., 1987; Lin et al., 1988a, 1988b; Krishnan et al., 1986; Okita et al., 1990) and there is strong evidence to suggest that the heterotetramer is the most active form of ADPGPP. Support for this suggestion comes from the isolation of plant "starchless" routants that are deficient in either of the subunits (Tsai and Nelson, 1966; Dickinson and Preiss, 1969; Lin et al., 1988a, 1988b) and from the characterization of an "ADPGPP" homotetramer of small subunits that was found to have only low enzyme activity (Lin et al., 1988b). In addition, proposed effector interaction residues have been identified for both subunits (Morell et al., 1988). Direct evidence for the active form of the enzyme and further support of the kinetic data reported for the purified potato enzyme comes from the expression of potato ADPGPP activity in E. coli and the comparison of the kinetic properties of this material and that from potato tubers (Iglesias et al., 1993).

Unregulated enzyme variants of the plant ADPGPP are identified and characterized in a manner similar to that which resulted in the isolation of the E. coli glgC16 and related mutants such as glgC-SG5 and CL1136. A number of plant ADPGPP cDNA's, or portions of such cDNA's, for both the large and small subunits, have been cloned from both monocots and dicots (Anderson et al., 1989a; Olive et al., 1989; Muller et al., 1990; Bhave et al., 1990; du Jardin and Berhin, 1991; Smith-White and Preiss, 1992). The proteins encoded by the plant cDNA's, as well as those described from bacteria, show a high degree of conservation (Bhave et al., 1990). In particular, a highly conserved region, also containing some of the residues implicated in enzyme function and effector interactions, has been identified (Morell et al., 1988; du Jardin and Berhin, 1991). Clones of the potato tuber ADPGPP subunit genes have been isolated. These include a complete small subunit gene, assembled by addition of sequences from the first exon of the genom/c clone with a nearly full-length cDNA clone of the same gene, and an almost complete gene for the large subunit. The nucleotide sequence (SEQ ID NO:7) and the amino acid sequence (SEQ ID NO:8) of the assembled small subunit gene is given below. The nucleotide sequence presented here differs from the gene originally isolated in the following ways: a BglII+NcoI site was introduced at the ATG codon to facilitate the cloning of the gene into E. coli and plant expression vectors by site directed mutagenesis utilizing the oligonucleotide primer sequence GTTGATAACAAGATCTGTTAAC CATGGCGGCTTCC (SEQ ID NO: 11 ).

A SacI site was introduced at the stop codon utilizing the oligonucleotide primer sequence CCAGTTAAAACGGAGCTCATCAGATGATGATTC (SEQ ID NO:12).

The SacI site serves as a 3' cloning site. An internal BglII site was removed utilizing the oligonucleotide primer sequence GTGTGAGAACATAAATCTTGGATATGTTAC (SEQ ID NO:13).

This assembled gene was expressed in E. coli under the control of the recA promoter in a PrecA-gene10L expression cassette (Wong et al., 1988) to produce measurable levels of the protein. An initiating methionine codon is placed by site-directed mutagenesis utilizing the oligonucleotide primer sequence
GAATTCACAGGGCCATGGCTCTAGACCC (SEQ ID NO: 14)
to express the mature gene.

The nucleotide sequence (SEQ ID NO:9) and the amino acid sequence (SEQ ID NO:10) of the almost complete large subunit gene is given below. An initiating methionine codon has been placed at the mature N-terminus by site-directed mutagenesis utilizing the oligonucleotide primer sequence A A G A T C A A A C C T G C C A T G G C T T A C T CT-GTGATCACTACTG (SEQ ID NO:15). The purpose of the initiating methionine is to facilitate the expression of this large subunit gene in *E. coli*. A HindIII site is located 103 bp after the stop codon and serves as the 3' cloning site. The complete large ADPGPP gene is isolated by the 5' RACE procedure (Rapid Amplification of cDNA Ends; Frohman, 1990; Frohman et al., 1988; Loh et al., 1989). The oligonucleotide primers for this procedure are as follows:

1) GGGAATTCAAGCTTGGATCCCGGGC-CCCCCCCCCCCCCC (SEQ ID NO:16);
2) GGGAATTCAAGCTTGGATCCCGGG (SEQ ID NO:17); and
3) CCTCTAGACAGTCGATCAGGAGCAGATGTACG (SEQ ID NO:18).

The first two are the equivalent to the ANpolyC and the AN primers of Loh et al. (1989), respectively, and the third is the reverse complement to a sequence in the large ADPGPP gone. The PCR 5' sequence products are cloned as EcoRI/HindIII/BamHI-PstI fragments and are easily assembled with the existing gone portion.

The weakly regulated enzyme routants of ADPGPP are identified by initially scoring colonies from a routagonized *E. coli* culture that show elevated glycogen synthesis, by iodine staining of 24–48 hour colonies on Luria-Agar plates containing glucose at 1%, and then by characterizing the responses of the ADPGPP enzymes from these isolates to the positive and negative effectors of this activity (Cattaneo et al., 1969; Preiss et al., 1971). A similar approach is applied to the isolation of such variants of the plant ADPGPP enzymes. Given an expression system for each of the subunit genes, muta-genesis of each gone is carried out separately, by any of a variety of known means, both chemical or physical (Miller, 1972) on cultures containing the gone or on purified DNA. Another approach is to use a PCR procedure (Ehrlich, 1989) on the complete gone in the presence of inhibiting Mn++ions, a condition that leads to a high rate of misincorporation of nucleotides. A PCR procedure may also be used with primers adjacent to just a specific region of the gone, and this mutagenized fragment then recloned into the non-mutagenized gene segments. A random synthetic oligonucleotide procedure may also be used to generate a highly mutagenized short region of the gone by mixing of nucleotides in the synthesis reaction to result in misincorporation at all positions in this region. This small region is flanked by restriction sites that are used to reinsert this region into the remainder of the gene. The resultant cultures or transformants are screened by the standard iodine method for those exhibiting glycogen levels higher than controls. Preferably this screening is carried out in an *E. coli* strain deficient only in ADPGPP activity and is phenotypically glycogen-minus and that is complemented to glycogen-plus by glgC. The *E. coli* strain should retain those other activities required for glycogen production. Both genes are expressed together in the same *E. coli* host by placing the genes on compatible plasmids with different selectable marker genes, and these plasmids also have similar copy numbers in the bacterial host to maximize heterotetramer formation. An example of such an expression system is the combination of pMON17335 and pMON17336 (Iglesias et al., 1993). The use of separate plasmids enables the screening of a mutagenized population of one gone alone, or in conjunction with the second gone following transformation into a competent host expressing the other gene, and the screening of two mutagenized populations following the combining of these in the same host. Following re-isolation of the plasmid DNA from colonies with increased iodine staining, the ADPGPP coding sequences are recloned into expression vectors, the phenotype verified, and the ADPGPP activity and its response to the effector molecules determined. Improved variants will display increased $V_{max}$, reduced inhibition by the negative effector ($P_i$), or reduced dependence upon activator (3-PGA) for maximal activity. The assay for such improved characteristics involves the determination of ADPGPP activity in the presence of $P_i$ at 0.045 mM ($I_{0.5}$=0.045 mM) or in the presence of 3-PGA at 0.075 mM ($A_{0.5}$=0.075 mM). The useful variants will display <40% inhibition at this concentration of $P_i$ or display >50% activity at this concentration of 3-PGA. Following the isolation of improved variants and the determination of the subunit or subunits responsible, the mutation(s) are determined by nucleotide sequencing. The mutation is confirmed by recreating this change by site-directed mutagenesis and reassay of ADPGPP activity in the presence of activator and inhibitor. This mutation is then transferred to the equivalent complete ADPGPP cDNA gene, by recloning the region containing the change from the altered bacterial expression form to the plant form containing the amyloplast targeting sequence, or by site-directed mutagenesis of the complete native ADPGPP plant gene.

EXAMPLE 1

Construction of DNA Vectors for glgC16 Expression

To express the *E. coli* glgC16 gene in plant cells, and to target the enzyme to the plastids, the gene needed to be fused to a DNA encoding the plastid-targeting transit peptide (hereinafter referred to as the CTP/ADP-glucose pyrophosphorylase gene), and to the proper plant regulatory regions. This was accomplished by cloning the glgC16 gene into a series of plasmid vectors that contained the needed sequences.

The plasmid pLP226 contains the glgC16 gene on a HincII fragment, cloned into a pUC8 vector at the HincII site (Leung et al. 1986). pLP226 was obtained from Dr. Jack Preiss at Michigan State University, and was transformed into frozen competent *E. coli* JM101 cells, prepared by the calcium chloride method (Sambrook et al., 1989). The transformed cells were plated on 2XYT (infra) plates that contained ampicillin at 100 µg/ml. The plasmid pLP226 was purified by the rapid alkaline extraction procedure (RAE) from a 5 ml overnight culture (Birnboim and Doly, 1979).

To fuse the glgC16 gene to the DNA encoding the chloroplast transit peptide, a NcoI site was needed at the 5' end of the gene. A SacI site downstream of the termination codon was also needed to move the CTP/ADP-glucose pyrophosphorylase gene into the next vector. In order to introduce these sites, a PCR reaction (#13) was run using approximately 20 ng of rapid alkaline extraction-purified plasmid pLP226 for a template. The reaction was set up following the recommendations of the manufacturer (Perkin Elmer Cetus). The primers were QSP3 and QSP7. QSP3 was designed to introduce the NcoI site that would include the start codon for the glgC 16 gene. The QSP7 primer hybridized in the 3' nontranslated region of the glgC16 gene and added a SacI site. The Thermal Cycler was programmed for 30 cycles with a 1 min 94° C. denaturation step, a 2 min 50° C. annealing step, and a 3 min 72° C. extension step. After each cycle, the extension step was increased by 15 sec. QSP3 Primer: 5' GGAGTTAGCCATGGTTAGTTTAGAG 3' (SEQ ID NO: 19) QSP7 Primer:
5' GGCCGAGCTCGTCAACGCCGTCTGCGATTTGTGC 3' (SEQ ID NO: 20)

The PCR product was cloned into vector pGEM3zf+ (Promega, Madison, Wis.), which had been digested with SacI and Hind III and had the DNA for the modified Arabidopsis small subunit CTP ligated at the HindIII site. The DNA and amino acid sequences of this CTP are shown in SEQ ID NO: 5 and SEQ ID NO: 6, respectively.

The linearized vector was treated with 5 units of calf intestinal alkaline phosphatase for 30 min at 56° C. Then, both the vector and the PCR #13 fragment, which had the glgC16 gene with the new NcoI and SacI sites, were run on an agarose gel and the fragments were purified by binding to DEAE membranes. The protocol used for the fragment purification with the DEAE membrane is from Schleicher and Schuell, and is titled "Binding and Recovery of DNA and RNA Using S and S DEAE Membrane."

Ligation #5 fused the glgC16 gene to the DNA for the modified Arabidopsis SSU CTP with the pGEM3zf+. The ligation contained 3 µl of vector that had been digested with NcoI and SacI, along with 3 µl of the PCR #13 product, that had also been cut with NcoI and SacI and repurified on a gel. 5 µl (of 20 µl total) of ligation #5 was transformed into frozen competent JM101 cells, and the transformed cells were plated on 2XYT plates (16 g/l Bactotryptone, 10 g/l yeast extract, 10 g/l NaCl, pH 7.3, and solidified with 1.5% agar) containing ampicillin.

Sample 1 was picked from a plate after overnight growth. This sample was inoculated into 4 ml of 2XYT media and grown overnight at 37 ° C. The plasmid was isolated by the rapid alkaline extraction procedure, and the DNA was digested with EcoRI, NcoI, and EcoRI and NcoI together. The digest was separated on an agarose gel, and the expected fragments were observed. The plasmid isolated from sample 1 of was designated pMON20100, and consisted of pGEM3zf+, the DNA for the modified Arabidopsis SSU CTP, and the glgC16 gene. The fusion was in the orientation that allowed it to be transcribed from the SP6 polymerase promoter.

To test this construct for import of the ADPglucose pyrophosphorylase into isolated lettuce chloroplasts, the CTP/ADPglucose pyrophosphorylase fusion needed to be transcribed and translated to produce [$^{35}$S]-labeled ADPglucose pyrophosphorylase. To make a DNA template for transcription by the SP6 polymerase, the CTP/ADPglucose pyrophosphorylase region of pMON20100 was amplified by PCR to generate a large amount of linear DNA. To do this, about 0.1 µl of pMON20100, that had been purified by rapid alkaline extraction, was used as a template in PCR reaction #80. The primers were a commercially available SP6 promoter primer (Promega) and the oligo QSP7 (SEQ ID NO:20). The SP6 primer hybridized to the SP6 promoter in the vector, and included the entire SP6 promoter sequence. Therefore, a PCR product primed with this oligo will contain the recognition sequence for the SP6 polymerase. The QSP7 (SEQ ID NO:20) primer will hybridize in the 3' nontranslated region of the glgC16 gene. This is the same primer that was used to introduce a SacI site downstream of the glgC16 termination codon. The Thermal Cycler was programmed for 30 cycles with a 1 min denaturation at 94° C., a 2 min annealing at 55° C., and a 3 min extension at 72° C. After each cycle, 15 sec were added to the extension step. SP6 Promoter Primer: 5' GATTTAGGTGACACTATAG 3' (SEQ ID NO:21)

5 µl of PCR reaction #80 was run on an agarose gel and purified by binding to DEAE membrane. The DNA was eluted and dissolved in 20 µl of TE. 2 µl of the gel-purified PCR #80 product was used in an SP6 RNA polymerase in vitro transcription reaction. The reaction conditions were those described by the supplier (Promega) for the synthesis of large amounts of RNA (100 µl reaction). The RNA produced from the PCR reaction #80 DNA was used for in vitro translation with the rabbit reticulocyte lysate system (Promega). $^{35}$S-labeled protein made from pMON20100 (i.e., PCR reaction #80) was used for an in vitro chloroplast import assay as previously described. After processing the samples from the chloroplast import assay, the samples were subjected to electrophoresis on SDS-PAGE gels with a 3–17% polyacrylamide gradient. The gel was fixed for 20–30 min in a solution with 40% methanol and 10% acetic acid. Then, the gel was soaked in EN3HANCE™ for 20–30 min, followed by drying the gel on a gel dryer. The gel was imaged by autoradiography, using an intensifying screen and an overnight exposure. The results demonstrated that the fusion protein was imported into the isolated chloroplasts.

The construct in pMON20100 next was engineered to be fused to the enhanced CaMV 35S promoter (Kay, R. 1987) and the NOS 3' end (Bevan, M. 1983) isolated from pMON999. PCR reaction 114 contained plasmid pMON20100 as a template, and used primers QSM11 and QSM10. QSM11 annealed to the DNA for the modified Arabidopsis SSU CTP and created a BglII site 7 bp upstream from the ATG start codon. QSM10 annealed to the 3' end of the glgC16 gene and added an XbaI site immediately after the termination codon, and added a SacI site 5 bp after the termination codon. The SacI site that had earlier been added to the glgC16 gene was approximately 100 bp downstream of the rex-ruination codon. The Thermal Cycler was programmed for 25 cycles with a 1 min 94° C. denaturation, a 2 min 55° C. annealing, and a 3 min 72° C. extension step. With each cycle, 15 sec was added to the extension step. QSM11 Primer (SEQ ID NO:22):
5' AGAGAGATCTAGAACAATGGCTTCCTCTATGCTCTCTTCCGC 3'
QSM10 Primer (SEQ ID NO:23):
5' GGCCGAGCTCTAGATTATCGCTCCTGTTTATGCCCTAAC 3'

95µl (from 100 µl total volume) of PCR reaction #114 was ethanol precipitated, and resuspended in 20 µl of TE. 5 µl of this was digested with BglII (4 units) and SacI (10 units) overnight at 37° C. 5 µl (5 µg) of the vector, pMON999, which contains the enhanced CaMV 35S promoter and the NOS 3' end, was digested in the same manner. After digestion with the restriction enzymes, the DNAs were run on an agarose gel and purified by binding to DEAE membranes. Each of the DNAs were dissolved in 20 gl of TE. 1 µl of PCR 114 was ligated with 3 µl of the vector, in a total volume of 20 µl. The ligation mixture was incubated at 14° C. for 7 hr. 10 µl of the ligation was transformed into frozen competent MM294 cells and plated on LB plates (10 g/l Bactotryptone, 5 g/l yeast extract, 10 g/l NaCl, and 1.5% agar to solidify) with 100/µg/ml ampicillin. Colonies were picked and inoculated into tubes with 5 ml of LB media with 100 µg/ml ampicillin, for overnight growth. The 5 ml overnight cultures were used for rapid alkaline extractions to isolate the plasmid DNAs. The DNAs were digested with EcoRI, and separate aliquots were digested with NotI. After analyzing these samples on agarose gels, the plasmid pMON20102 was confirmed to have the 497 bp EcoRI fragment that is characteristic of the glgC16 gene. This plasmid also contained the 2.5 kb NotI fragment which contained the enhanced CaMV 35S promoter, the DNA for the modified Arabidopsis SSU CTP, the glgC16 gene, and the NOS 3' end.

The pMON20102 plasmid was then used to construct a DNA vector which would express the glgC16 gene in a tuber-specific manner and would be used for the transformation of potato. This construct causes specific expression of the ADPGPP in potato tubers and increases the level of starch in the tubers.

The vector used in the potato transformation is a derivative of the Agrobacterium mediated plant transformation vector pMON886. The pMON886 plasmid is made up of the following well characterized segments of DNA. A 0.93 kb fragment isolated from transposon Tn7 which encodes bacterial spectinomycin/streptomycin (Spc/Str) resistance and is a determinant for selection in E. coli and Agrobacterium tumefaciens (Fling et al., 1985). This is joined to a chimeric kanamycin resistance gene engineered for plant expression to allow selection of the transformed tissue. The chimeric gene consists of the 0.35 kb cauliflower mosaic virus 35S promoter (P-35S) (Odell et al., 1985), the 0.83 kb neomycin phosphotransferase type II gene (NPTII), and the 0.26 kb 3'-nontranslated region of the nopaline synthase gene (NOS 3') (Fraley et al., 1983). The next segment is a 0.75 kb origin of replication from the RK2 plasmid (ori-V) (Stalker et al., 1981). It is joined to a 3.1 kb SalI to PvuI segment of pBR322 which provides the origin of replication for maintenance in E. coli (ori-322) and the bom site for the conjugational transfer into the Agrobacterium tumefaciens cells. Next is a 0.36 kb PvuI fragment from the pTiT37 plasmid which contains the hopaline-type T-DNA right border region (Fraley et al., 1985).

The glgC16 gene was engineered for expression primarily in the tuber by placing the gene under the control of a tuber-specific promoter. The GlgC16 protein was directed to the plastids within the plant cell due to its synthesis as a C-terminal fusion with a N-terminal protein portion encoding a chloroplast targeting sequence (CTP) derived from that from the SSU 1A gene from Arabidopsis thaliana (Timko et al., 1989). The CTP portion is removed during the import process to liberate the GlgC16 enzyme. Other plant expression signals also include the 3' polyadenylation sequences which are provided by the NOS 3' sequences located downstream from the coding portion of the expression cassette. This cassette was assembled as follows: The patatin promoter was excised from the pBI241.3 plasmid as a HindIII-BamHI fragment (The pBI241.3 plasmid contains the patatin-1 promoter segment comprising from the AccI site at 1323 to the DraI site at 2289 [positions refer to the sequence in Bevan et al., 1986] with a HindIII linker added at the former and a BamHI linker added at the latter position; Bevan et al., 1986) and ligated together with the CTP1-glgC16 fusion (the BglII-SacI fragment from pMON20102) and pUC-type plasmid vector cut with HindIII and SacI (these cloning sites in the vector are flanked by NotI recognition sites). The cassette was then introduced, as a NotI site in pMON886, such that the expression of the glgC16 gene is in the same orientation as that of the NPTII (kanamycin) gene. This derivative is named pMON20113, illustrated in FIG. 7 of Kishore, WO 91/19806.

Plant Transformation/Regeneration

The pMON20113 vector was mobilized into disarmed Agrobacterium tumefaciens strain by the triparental conjugation system using the helper plasmid pRK2013 (Ditta et al., 1980). The disarmed strain ABI was used, carrying a Ti plasmid which was disarmed by removing the phytohormone genes responsible for crown gall disease. The ABI strain is the A208 Agrobacterium tumefaciens carrying the disarmed pTiC58 plasmid pMP90RK (Koncz and Schell, 1986). The disarmed Ti plasmid provides the trfA gene functions required for autonomous replication of the pMON vector after the conjugation into the ABI strain. When the plant tissue is incubated with the ABI::pMON conjugate, the vector is transferred to the plant cells by the vir functions encoded by the disarmed pMP90RK Ti plasmid.

The pMON20113 construct, encoding the bacterial ADPGPP gene (SEQ ID NO:1), was transformed into the Russet Burbank potato variety Williams by the following procedure. To transform Russet Burbank potatoes, sterile shoot cultures of Russet Burbank are maintained in sundae cups containing 8 ml of PM medium supplemented with 25 mg/L ascorbic acid (Murashige and Skoog (MS) inorganic salts, 30 g/l sucrose, 0.17 g/l $NaH_2PO_4H_2O$, 0.4 mg.l thiamine-HCl, and 100 mg/l myo-inositol, solidified with 2 g/l Gelrite at pH 6.0). When shoots reach approximately 5 cm in length, stem internode segments of 3-5 mm are excised and inoculated with a 1:10 dilution of an overnight culture of Agrobacterium tumefaciens from a 4 day old plate culture. The stem explants are co-cultured for 2 days at 20° C. on a sterile filter paper placed over 1.5 ml of a tobacco cell feeder layer overlaid on 1/10 P medium (1/10 strength MS inorganic salts and organic addenda without casein as in Jarret et al. (1980), 30 g/l sucrose and 8.0 g/l agar). Following co-culture, the explants are transferred to full strength P-1 medium for callus induction, composed of MS inorganic salts, organic additions as in Jarret et al. (1980), with the exception of casein, 5.0 mg/l zeatin riboside (ZR), and 0.10 mg/l naphthalene acetic acid NAA (Jarret et al., 1980a, 1980b). Carbenicillin (500 mg/l) and cefotaxime (100 mg/L) are included to inhibit bacterial growth, and 100 mg/l kanamycin is added to select for transformed cells.

After 4 weeks, the explants are transferred to medium of the same composition, but with 0.3 mg/l gibberellic acid (GA3) replacing the NAA (Jarret et al., 1981) to promote shoot formation. Shoots begin to develop approximately 2 weeks after transfer to shoot induction medium. These shoots are excised and transferred to vials of PM medium for rooting. After about 4 weeks on the rooting medium, the plants are transferred to soil and are gradually hardened off. Shoots are tested for kanamycin resistance conferred by the enzyme neomycin phosphotransferase II, by placing the shoots on PM medium for rooting, which contains 50 mg/L kanamycin, to select for transformed cells.

Russet Burbank Williams plants regenerated in culture were transplanted into 6 inch (~15.24 cm) pots and were grown to maturity under greenhouse conditions. Tubers were harvested and were allowed to suberize at room temperature for two days. All tubers greater than 2 cm. in length were collected and stored at 3° C. under high humidity.

Specific Gravity and Starch Determinations of Stored Tubers

Specific gravity (SG) was determined after 3 and 4 months of cold (3 ° C.) storage for the largest 2 or 3 tubers from each plant, with typical weights being 20–40 grams per tuber. Tubers were allowed to warm to room temperature for a few hours prior to specific gravity determination, but were not allowed to recondition. Specific gravity calculations were performed by the weight in air/weight in water method, where SG =weight in air/(weight in air–weight in water). Calculations for percent starch and percent dry matter based on SG were according to the following formulas (yon Scheele, 1937):

% starch=17.546+(199.07)(SG−1.0988)

% dry matter=24.182+(211.04)(SG−1.0988)

Starch analysis was performed on fresh, center sections of stored tuber tissue as described (Lin et al., 1988). Tubers were not allowed to warm before harvesting tissue. Briefly, approximately 100 mg. center sections were cut, weighed, placed in 1.5 ml centrifuge tubes, and frozen on dry ice. The tissue was then dried to a stable weight in a Savant Speed-Vac Concentrator, and final dry weight was determined. Soluble sugars were first removed by extracting three times with 1 ml. of 80% ethanol at 70 ° C., for 20 minutes per treatment. After the final incubation, all remaining ethanol was removed by desiccation in a Speed- Vac Concentrator. The solid material was resuspended in 400 µl 10.2M potassium hydroxide, ground, and then incubated for 30 min. at 100 ° C to solubilize the starch. The solutions were cooled and neutralized by addition of 80 µl 1N acetic acid. Starch was degraded to glucose by treatment with 14.8 units of pancreatic alpha-amylase (Sigma Chemical, St. Louis) for 30 min. at 37° C., followed by 10 units of amyloglucosidase (Sigma Chemical, St. Louis) for 60 min. at 55 ° C. Glucose released by the enzymatic digestions was measured using the Sigma (St. Louis) hexokinase kit, and these values were used to calculate starch content.

Sugar Analysis

Tubers were stored at 3° C. and were not allowed to recondition at room temperature prior to sugar analysis. Center cuts from stored tubers were obtained, fresh weights determined, and the tissue was frozen on dry ice prior to desiccation in Savant Speed-Vac Concentrator. Approximate fresh weight per sample was 100 mg. Dry tuber material was coarsely ground, and sugars were extracted three times with 0.5 ml 80% ethanol at 70 ° C. for 20 minutes per extraction. After each incubation, the insoluble material was spun down for 2 minutes in a microcentrifuge and the supernatant collected. The supernatants from all three extractions were combined, dried down, and resuspended in 1 ml 100 mM Tris buffer, pH 7.5. For each sugar analysis, 10µl of sample was used.

For each sample, glucose content was determined using a Glucose [HK] diagnostic kit (Sigma Chemical Co., St. Louis, Mo.) according to manufacturers protocol. Briefly, 1 mL of reconstituted reagent was incubated with 10 µl of sample at room temperature for 10 minutes, and the sample concentration determined by measuring absorbance at 340 nm subtracting the absorbance of 10 µl of sample in water. Percent glucose was then calculated by the equation:

% glucose=[($A_{340}$×2.929)/mg. fresh weight]×100%

Fructose content was determined by adding 1µg of phosphoglucoisomerase to the above reaction for glucose determination, and subtracting the resultant percent glucose+fructose value from percent glucose. Sucrose content was determined by addition of 1 µg phosphoglucoisomerase and 100 µg yeast invertase to the glucose HK assay, and extending incubation time to 30 minutes at room temperature. Percent sucrose was determined as above, subtracting the values obtained for glucose and fructose content.

Western Blot Analysis of Stored Tubers

Tubers stored at 3 ° C. were not allowed to warm prior to isolation of tissue for analysis. For Western blot analysis, proteins were extracted from desiccated, coarsely powdered tuber tissue by grinding 1:1 in 100 mM Tris pH 7.5, 35 mM KCl 5 mM dithiothreitol, 5 mM ascorbate, 1 mM EDTA, 1 mM benzamidine, and 20% glycerol. The protein concentration of the extract was determined using the Pierce BCA method, and proteins were separated on 3–17% SDS polyacrylamide gels (Laemmli, 1970). *E. coli* ADPGPP was detected using goat antibodies raised against purified *E. coli* ADPGPP and alkaline phosphatase conjugated rabbit anti-goat antibodies (Promega, Madison, Wis.).

Fry Color Determination

Eight transgenic potato lines expressing the *E. coli* glgC16 gene, and 20 control lines consisting of a combination of lines from the pMON20113 transformation event which do not express the *E. coli* glgC16 gene, and several nontransgenic Russet Burbank control lines, were grown under field conditions in Parma, Id. Tubers were harvested and stored for two months at 40 ° C. Fry color was determined for all potato lines by taking center cuts from representative samples from each line and frying at 375 ° F. in soybean oil for 3 minutes and 30 seconds. Fry color was determined by photovoltaic measurement and values were reported according to the USDA color class chart for frozen french fries.

Results

All tubers were harvested from plants of the same variety (Russet Burbank Williams 82), the same age, and grown side by side under identical growth conditions. Western blot analysis showed that levels of *E. coli* ADPGPP were essentially equivalent to levels determined at harvest (Table 1), suggesting that the levels of *E. coli* ADPGPP protein are stable during cold storage. Analysis of tubers stored at 3° C. under high humidity shows that those expressing the *E. coli* glgC16 gene accumulate 5 - to 6-fold less reducing sugar than do control tubers (Tables 2, 3, 4, 5, and 6). Sucrose levels were comparable between control and transgenic tubers, while starch levels were significantly higher in the transgenic tubers. These results suggest that as starch is degraded during storage, the sugars formed tend to be resynthesized into starch in those tubers expressing the *E. coli* glgC16 gene, while in control tubers the sugars tend to accumulate.

Transgenic potato plants expressing the *E. coli* glgC16 gene have been grown under field conditions and tubers from GlgC16 potato lines were stored at 40° F. (4° C.) along with tubers from several different control lines. Fry color, which directly correlated with sugar content, was determined after two months cold storage. The average fry color in the transgenic potato tubers was significantly improved (lighter) relative to that in control tubers (darker color) stored under identical conditions (Table 7), demonstrating that sugar levels were lower in the tubers expressing the *E. coli* glgC16 gene. Direct measurement of reducing sugar content in a sample of the field grown tubers stored for 14 weeks at 3° C. supports the fry color results in that tubers expressing the *E. coli* glgC16 gene contained significantly less reducing sugar than controls (Table 8). Tubers from transgenic potato plants were tested for rate and degree of reconditioning following cold storage. The fry color of transgenic lines which produce tubers having a specific gravity greater than 1.083 indicated an increased rate and degree of reconditioning at 65° F. as compared to controls (Table 9).

TABLE 1

Expression of *E. coli* ADPGPP in potato tubers at harvest and after 3 months cold storage. *E. coli* ADPGPP levels were estimated from Western blot analysis by comparison to known standards. Values are given in ng GlgC16 per 50 μg extracted tuber protein.

| Line | ng GlgC16 Harvest | ng GlgC16 3 Months |
|---|---|---|
| 353c | 20–25 | 20–25 |
| 535c | 25–30 | 20–25 |
| 448a | 25–30 | 25–30 |
| 182a | 2 | 0.5–1 |
| 199a | 20–25 | 20–25 |
| 288c | 20–25 | 20–25 |
| 194a | 15–20 | 15–20 |
| 524a | 10 | 15–20 |

TABLE 2

Sugar and starch content (Dry Weight measurements) in 3 month cold stored tubers. Reducing sugars are glucose and fructose, and total sugars are reducing sugars plus sucrose. Values (percent dry weight) represent the averages from 9 glgC16 + high starch potato lines, and 11 control (glgC16−) potato lines stored for 3 months at 3° C.

| | Reducing Sugars | Sucrose | Total Sugars | Starch |
|---|---|---|---|---|
| glgC16+ | 1.5 | 1.2 | 2.6 | 59.5 |
| Control | 7.0 | 0.8 | 7.8 | 53.7 |

TABLE 3

Sugar and starch content (Fresh Weight measurements) in 4 month cold stored tubers. Reducing sugars are glucose and fructose, and total sugars are reducing sugars plus sucrose. Values (percent fresh weight) represent the average from glgC16 + high starch potato lines, and 11 control (glgC16−) potato lines stored for 4 months at 3° C.

| | Reducing Sugars | Sucrose | Total Sugars | Starch |
|---|---|---|---|---|
| glgC16+ | 0.1 | 0.1 | 0.3 | 9.9 |
| Control | 0.8 | 0.2 | 1.0 | 6.0 |

TABLE 4

Reducing sugar content of potato tubers after 4 months cold storage. Numbers of plant lines containing sugar levels within the ranges shown are reported. Percentages are based on fresh weight.

| | Percent Reducing Sugar | | | | | |
|---|---|---|---|---|---|---|
| | 0–.2 | .2–.4 | .4–.6 | .6–.8 | .8–1.0 | 1.0+ |
| Control lines | 0 | 2 | 0 | 4 | 2 | 3 |
| glgC16 lines | 6 | 3 | 0 | 0 | 0 | 0 |

TABLE 5

Total sugar content of potato tubers after 4 months cold storage. Numbers of plant lines containing sugar levels within the ranges shown are reported. Percentages are based on fresh weight.

| | Percent Total Sugars | | | | | |
|---|---|---|---|---|---|---|
| | 0–1 | 1–2 | 2–3 | 3–4 | 4–5 | 5+ |
| Control lines | 0 | 0 | 0 | 2 | 3 | 6 |
| glgC16 lines | 3 | 4 | 2 | 0 | 0 | 0 |

TABLE 6

Starch content of potato tubers after 4 months cold storage. Numbers of plant lines containing starch levels within the ranges shown are reported. Percentages are based on fresh weight.

| | Percent Starch | | | | | |
|---|---|---|---|---|---|---|
| | 2–4 | 4–6 | 6–8 | 8–10 | 10–12 | 12–14 |
| Control lines | 1 | 6 | 3 | 1 | 0 | 0 |
| glgC16 lines | 0 | 0 | 2 | 3 | 3 | 1 |

TABLE 7

Average fry color of field grown tubers after 2 months cold storage at 40° F.. The fry color rating was assigned according to the USDA published color standards for frozen fried potatoes. In this rating, 0 = very light color and 4 = very dark color. Numbers of plant lines having fry colors within the ranges shown are reported.

| | Fry Color Rating | | | |
|---|---|---|---|---|
| | 2–2.49 | 2.5–2.99 | 3.0–3.49 | 3.5–4.0 |
| Control lines | 0 | 0 | 4 | 16 |
| glgC16 lines | 1 | 1 | 6 | 0 |

TABLE 8

Reducing sugar content of field grown potato tubers after 14 weeks storage at 3° C.. Numbers of plant lines containing sugar levels within the ranges shown are reported. Percentages are based on fresh weight.

| | Percent Reducing Sugars | | | |
|---|---|---|---|---|
| | 0.5–1 | 1–1.5 | 1.5–2 | 2–2.5 |
| Control lines | 0 | 4 | 2 | 2 |
| glgC16 lines | 4 | 2 | 2 | 0 |

EXAMPLE 2

Following storage at low temperatures, potatoes are frequently unacceptable for frying due to elevated sugar levels. These stored potatoes are improved by treatments such as blanching or reconditioning; the former treatment removes sugars by treatment of the potato slices with hot water and in the latter the sugars are metabolized during storage of the tubers at higher temperatures (~65 ° F.). Blanching is used to inactivate enzymes primarily but when sugars are high the times employed in this step are extended to many times the normal. The extension of this step results in lower recovery of product, a loss of flavor, is time consuming, requires high energy input, and produces waste material with high biological oxygen demand and thus poses additional limitations on the disposal of the waste water. Reconditioning requires additional controlled temperature storage facilities and optimal results may require a number of steps at different temperatures. Sprouting and incidence of disease will increase at the higher temperatures and with time. The fry color of fries made from cold-stored GlgC16 tubers were frequently lower (better) than controls and in some cases were low enough even after 3–4 months that no reconditioning would be required. These tests have been extended to tubers stored for 2 months at 50° F. and then for 3 months at 38° F. and include a measure of the rate of reconditioning also.

Tubers from plants transformed with the following vectors were tested: pMON17316 (with the patatin 3.5 promoter) and pMON17279 (with the small subunit of potato ADPGPP); as well as tubers from plants containing the patatin 1.0 promoter/glgC16 vector described above. These vectors were constructed as follows:

The patatin 3.5 promoter was obtained from the plasmid pPBI240.7 (Bevan, 1986). The majority of the 3.5 promoter was excised from pPBI240.7, from the HindIII site (−3500) to the XbaI site at −337, and combined with the remainder of the promoter, from the XbaI site to a BglII site at +22 (formerly a DraI site), in a triple ligation into a vector which provided a BglII site to form pMON17280. This latter plasmid then served as the vector for the triple ligation of the complete 3.5 promoter and the plastid target peptide-GlgC16 fusion from pMON20102, described above to form the tuber expression cassette (in pMON17282). This cassette, consisting of the patatin 3.5 promoter, the plastid target peptide-GlgC16 fusion, and the NOS 3' sequences, was introduced into the plant transformation vector pMON17227, a Ti plasmid vector disclosed and described by Barry et al. in WO 92/04449 (1991), incorporated herein by reference, on a NotI fragment to form pMON17316. See FIG. 1.

Figure 2:
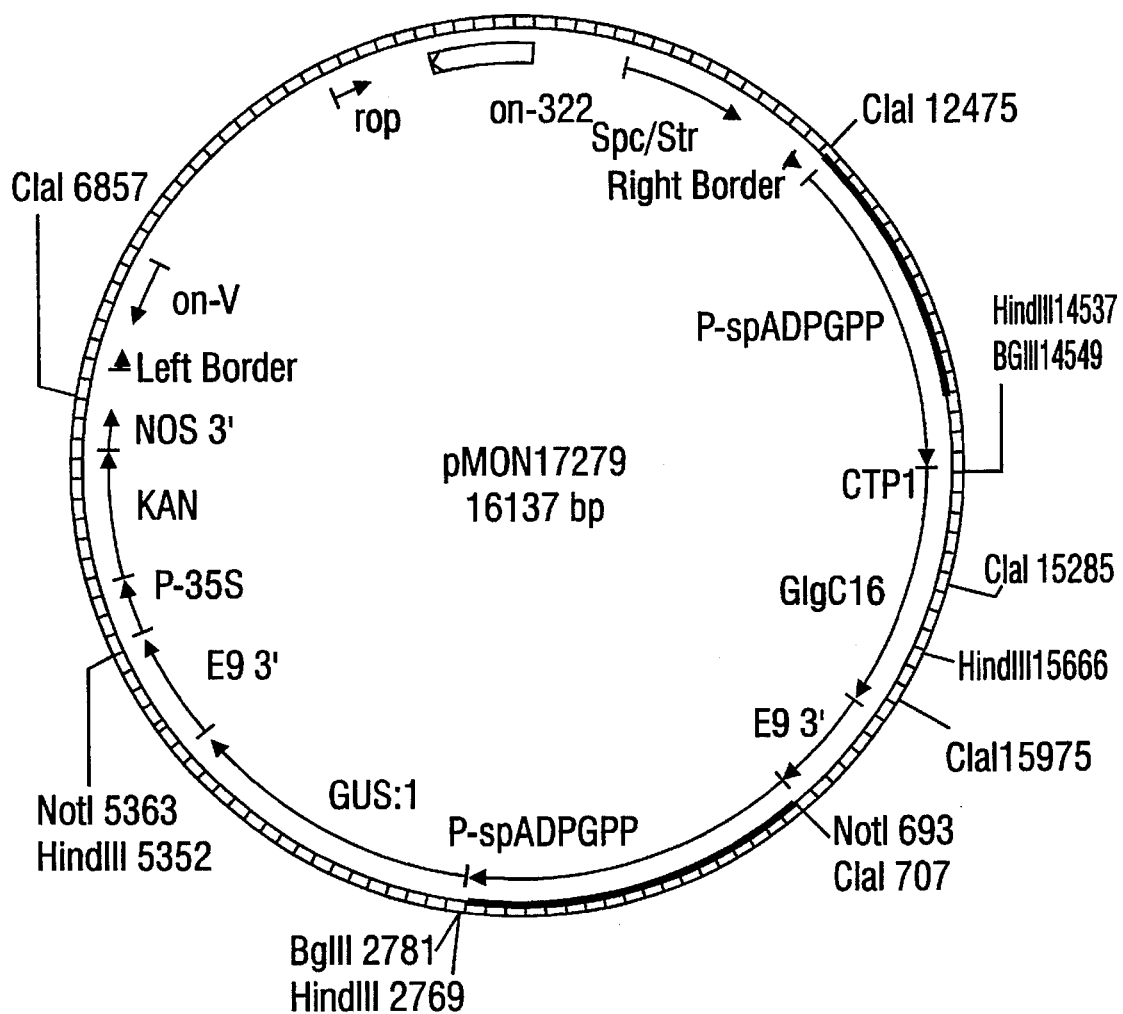
FIG. 2 shows a plasmid map for plant transformation vector pMON17279.

The promoter for the potato tuber ADPGPP small subunit gene, SEQ ID NO:24, was obtained as a XbaI-BglII fragment of the genomic clone 1–2 and inserted into the XbaI and BamHI site of Bluescript II KS- (Nakata et al., 1992). The promoter fragment used consists of the portion from the ClaI site about 2.0 kb 5' from the putative initiation methionine and extending to the HindIII site located 12 bp before this ATG. A BglII site was placed adjacent to this HindIII site by subcloning through another pUC vector, and was linked through this latter site to the fusion of the CTP targeting and the glgC16 coding sequences. This cassette, with a plant 3' recognition sequence was cloned into plant transformation vectors to form pMON17279 (also includes a cassette in which the E. coli uidA [GUS] gene is expressed from the same small potato 5 ADPGPP promoter). See FIG. 2.

These vectors were inserted into potato cells by Agrobacterium transformation followed by glyphosate selection. To transform potatoes using glyphosate as a selectable agent, the appropriate Agrobacterium was grown overnight in 2 ml of LBSCK. The following day, the bacteria was diluted 1:10 with MSO or until an optical density reading of 0.2–0.33 was established. Leaves from the stems of potato plants that had been grown under sterile conditions for three weeks on PM media supplemented with 25 mg/ml ascorbic acid were removed, stems were cut into 3–5 mm segments and inoculated with diluted bacteria as described previously. Explants were placed onto prepared co-culture plates. The co-culture plates contained 1/10 MSO with 1.5 mL of TxD cells overlain with wetted filter paper. About 50 explants were placed per plate. After 2 days co-culture period, explants were placed onto callus induction media which contains 5.0 mg/l Zeatin Riboside, 10 mg/l AgNO3 and 0.1 mg/l NAA for 2 days. Explants were subsequently transferred onto callus induction media which contained 0.025 mM glyphosate for selection. After 4 weeks, explants were placed onto shoot induction media which contained 5.0 mg/l Zeatin Riboside+ 10 mg/l AgNO3 and 0.3 mg/l GA3, with 0.025 mM glyphosate for selection. Shoots began to appear at 8 weeks. Explants were transferred to fresh shoot induction media every 4 weeks for 12 weeks. Shoots were excised and placed on PM media for about 2 weeks or until they were large enough to be placed into soil.

The data for GlgC16 Russet Burbank lines, including those expressing GlgC16 from the patatin 1.0 (HS01; HS03; MT01), patatin 3.5 (HS13), and the small subunit of potato ADPGPP (HS10) promoters is presented below (Table 9). A number of GlgC16 potato (variety Atlantic) lines were also examined (MT01; patatin 1.0 promoter). A processor would typically have to blanch to make acceptable products at a score of 2.0 or above. A number of Russet Burbank GlgC16 lines gave a fry score less than 2.0 immediately out of cold storage and thus could be processed directly. A fry color score of less than 2.0 is obtained with a large number of the lines after a very short period of reconditioning. This improved reconditioning response is seen for lines with increased solids and also for GlgC16 lines that did not show an increase in specific gravity. The improvement is also shown with all of these promoters used to express GlgC16 in the tuber. The effect of obtaining lines that may be fried directly out of storage and that recondition rapidly is also shown for GlgC16 Atlantic. Line MT01-27 also demonstrated that increased starch in the tuber is not necessary to obtain enhanced cold storage properties since the specific gravity of the lines tested was not significantly different from that of the Atlantic control.

TABLE 9

Fry Color/Reconditioning response of potatoes containing GlgC16. (Fry color rated according to USDA chart on a scale of 0–4; lowest–highest).

| Line | Number of days at 65° F. | | | | | |
|---|---|---|---|---|---|---|
|  | 0 | 3 | 6 | 10 | 13 | 17 |
| Control - Russet Burbank | | | | | | |
| RB02 | 2.2 | 2.3 | 1.8 | 2.0 | 1.0 | 1.3 |
| RB03 | 3.5 | 3.3 | 2.5 | 1.7 | 2.3 | 2.5 |
| RB05 | 2.3 | 2.5 | 2.2 | 2.0 | 1.2 | 1.3 |
| GlgC16 Russet Burbank | | | | | | |
| HS13-47* | 3.0 | 2.5 | 0.7 | 0.7 | 1.3 | 1.3 |
| HS10-15* | 1.3 | 1.3 | 0.4 | 0.8 | 1.0 | 1.0 |
| HS13-50* | 3.2 | 1.0 | 0.5 | 1.0 | 1.2 | 0.8 |
| MT01-82* | 2.2 | 1.2 | 0.7 | 1.0 | 1.5 | 1.0 |
| HS13-36* | 2.2 | 1.3 | 0.7 | 1.2 | 1.2 | 0.8 |
| HS10-20* | 1.0 | 0.7 | 0.5 | 0.5 | 0.4 | 0.5 |
| *-specific gravity greater than 1.083 | | | | | | |
| HS01-58# | 2.8 | 2.5 | 1.3 | 0.7 | 1.5 | 1.8 |
| HS03-20# | 3.2 | 2.3 | 1.7 | 2.8 | 1.8 | 2.0 |
| HS03-18# | 2.0 | 1.8 | 1.7 | 0.7 | 1.3 | 1.3 |
| HS03-12A# | 3.3 | 2.5 | 2.7 | 2.2 | 2.2 | 0.8 |
| HS03-12B# | 3.0 | 3.2 | 2.0 | 2.7 | 1.3 | 2.0 |
| HS01-49# | 2.2 | 1.3 | 2.3 | 2.2 | 1.5 | 0.8 |
| HS13-30# | 3.2 | 2.3 | 2.0 | 2.8 | 1.7 | 3.0 |
| #-specific gravity less than 1.083 | | | | | | |
| Control - Atlantic | | | | | | |
| AT-1 | 2.3 | 2.3 | 2.3 | 1.5 | 1.5 | 1.8 |
| GlgC16 Atlantic | | | | | | |
| MT01-24 | 2.5 | 1.8 | 2.8 | 1.2 | 2.2 | 1.3 |
| MT01-27 | 1.0 | 0.5 | 1.3 | 0.3 | 0.8 | 0.7 |

EXAMPLE 3

The effect of GlgC16 on delaying sprouting was tested on a population of tubers stored at 60° F. (these tubers had been stored previously at 38°–40° F. for 3 months). The tubers (4-6) were examined at intervals and scored for the presence of sprouts of >0.5 cm (Table 10). The delay in sprouting, represented as the number of days to 50% sprouted, was frequently improved in the GlgC16 lines, was observed in the three varieties tested (Russet Burbank, Atlantic, and Norchip); was observed in lines where GlgC16 was expressed from the patatin 1.0 (HS01, HS03, and MT01), the patatin 3.5 (HS13), and the potato small ADPGPP (HS10) promoters; and was seen in lines with and without increased solids content. The lines with the delay sprouted normally when planted in soil.

TABLE 10

| Variety | Line | Number of days to 50% sprouted |
|---|---|---|
| Russet Burbank | Control | 15 |
| | Control | 14 |
| | Control | 9 |
| | HS01-25 | 11 |
| | HS01-49 | 15 |
| | HS01-58 | 18 |
| | HS03-3 | 12 |
| | HS03-5 | 13 |
| | HS03-17 | 13 |
| | HS03-26 | 14 |
| | HS03-27 | 12 |
| | HS03-41 | 24 |
| | HS10-10 | 14 |
| | HS10-15 | 26 |
| | HS10-20 | >43† |
| | HS13-2 | 11 |
| | HS13-13 | 16 |
| | HS13-23 | 23 |
| | HS13-30 | 15 |
| | HS13-34 | 25 |
| | HS13-37 | 12 |
| | HS13-47 | 21 |
| | HS13-50 | 19 |
| | HS13-68 | 13 |
| | HS13-70 | 24 |
| | MT01-10 | 14 |
| | MT01-11 | 13 |
| | MT01-30 | 14 |
| | MT01-37 | 19 |
| | MT01-82 | 16 |
| Atlantic | Control | 6 |
| | MT01-6 | 11 |
| | MT01-7 | 9 |
| | MT01-15 | 10 |
| | MT01-31 | 6 |
| Norchip | Control | 8 |
| | MT01-1 | 12 |
| | MT01-5 | 13 |

†duration of observation; tubers from this line sprouted when planted in soil.

EXAMPLE 4

Additional tests were performed with potatoes transformed with glgC16 under the control of two different promoters. Promoters for the large subunit of potato tuber ADPGPP were isolated from two varieties of potato, Russet Burbank (SEQ ID NO:25) and Desiree (SEQ ID NO:26). The clones were identified using plaque hybridization with a probe from the 5' end of a cDNA from the large subunit of ADPglucose pyrophosphorylase. The translational start sites (ATG) of these clones were identified by plant consensus (Lutcke et al., 1987). PCR primers were used to introduce an BAMHI site at the 3' end downstream of the ATG and a HINDIII site at the 5' end of both promoters. The resulting 600 bp Russet Burbank promoter and 1600 bp Desiree promoters were ligated independently into pMON10098 in place of the E35S promoter, and fused with a BglII-SacI fragment from pMON20102 containing CTP-glgC16 chimeric gene. The E35S-NPTII-Nos cassette was removed from these plasmids and replaced with a NotI- SalI fragment containing the FMV-CTP-CP4-E9 cassette of pMON17227, discussed above, resulting in pMON21522 (Russet Burbank-derived promoter) and pMON21523 (Desiree-derived promoter). The pMON10098 plasmid contains the following DNA regions: 1) The chimeric kanamycin resistance gene engineered for plant expression to allow selection of the transformed tissue. The chimeric gene consists of the 0.35 Kb cauliflower mosaic virus 35S promoter (P-35S) (Odell et al., 1985), the 0.83 Kb NPTII gene, and the 0.26 Kb 3'-nontranslated region of the NOS 3'; 2) The 0.45 Kb ClaI to the DraI fragment from the pTi15955 octopine Ti plasmid, which contains the T-DNA left border region (Barker et al., 1983); 3) The 0.75 Kb segment containing the origin of replication from the RK2 plasmid (ori-V) (Stalker et al., 1981); 4) The 3.0 Kb SalI to PstI segment of pBR322 which provides the origin of replication for maintenance in *E. coli* (ori-322), and the bom site for the conjugational transfer into the *Agrobacterium tumefaciens* cells; 5) The 0.93 Kb fragment isolated from transposon Tn7 which encodes bacterial spectinomycin/streptomycin resistance (Spc/Str) (Fling et al., 1985), and is a determinant for selection in *E. coli* and *Agrobacterium tumefaciens*; 6) The 0.36 Kb PvuI to BclI fragment from the pTiT37 plasmid, which contains the nopaline-type T-DNA right border region (Fraley et al., 1985); and 7) The last segment is the expression cassette consisting of the 0.65 Kb cauliflower mosaic virus (CaMV) 35S promoter enhanced by duplication of the promoter sequence (P-E35S) (Kay et al., 1987), a synthetic multilinker with several unique cloning sites, and the 0.7 Kb 3' nontranslated region of the pea rbcS-E9 gene (E9 3') (Coruzzi et al., 1984). The plasmid was mated into *Agrobacterium tumefaciens* strain ABI, using the triparental mating system, and used to transform Russet Burbank line Williams 82.

The improvements in storage characteristics have also been shown for Russet Burbank transformed with pMON22152 and pMON21523, in which GlgC16 is expressed from promoters for the large subunit of potato tuber ADPGPP. Field grown tubers were stored initially, after harvest for 1 month at 50° F., after which they were placed in cold storage at 40° F. for 4 months. In one test, the fry color of fries produced from these tubers directly out of storage was evaluated by determining the reflectance of the fried material; lower values are preferred. In second test, a portion of the cold stored tubers were transferred to 55° F. to determine the response in reconditioning. The data for these evaluations, for both the stem and bud ends of the tubers are presented in Table 11. In both cases, many lines have better color values than the controls, both for direct frying and following reconditioning. For instance, pMON21522-144, pMON21523-79, and many others show dramatic improvements over the controls.

TABLE 11

| | Reflectance of fried strips[1,2] | | | |
|---|---|---|---|---|
| | 40° F. Storage[3] | | 40° F. Storage: 21 d.@ 55° F.[4] | |
| LINE # | Bud[5] | Stem[5] | Bud | Stem |
| pMON21522 | | | | |
| 144 | 24.3 | 22.1 | 34.6 | 25.4 |
| 209 | 22.8 | 20.1 | 31.4 | 23.2 |
| 149 | 27.1 | 22.4 | 30.7 | 27.5 |

TABLE 11-continued

| | Reflectance of fried strips[1,2] | | | |
|---|---|---|---|---|
| | 40° F. Storage[3] | | 40° F. Storage: 21 d.@ 55° F.[4] | |
| LINE # | Bud[5] | Stem[5] | Bud | Stem |
| 178 | 25.3 | 21.1 | 34.9 | 29.3 |
| 194 | 23.7 | 20.8 | 30.6 | 23.5 |
| 204 | 21.3 | 14.7 | 33.9 | 23.0 |
| 218 | 22.8 | 18.9 | 33.3 | 20.7 |
| Control/Mean[6] pMON21523 | 19.7 | 16.8 | 31.0 | 25.1 |
| 33 | 22.1 | 16.5 | 29.8 | 23.1 |
| 34 | 21.2 | 18.2 | 32.1 | 27.3 |
| 38 | 24.0 | 23.2 | 28.3 | 23.6 |
| 40 | 24.4 | 15.3 | 31.5 | 26.2 |
| 47 | 22.0 | 15.6 | 34.9 | 27.7 |
| 48 | 23.0 | 19.3 | 31.1 | 24.9 |
| 79 | 24.4 | 19.7 | 35.8 | 29.7 |
| 80 | 21.8 | 20.5 | 32.7 | 25.5 |
| 93 | 20.7 | 17.4 | 31.1 | 23.2 |
| 99 | 19.8 | 17.1 | 30.6 | 23.4 |
| 31 | 22.1 | 21.6 | 30.2 | 24.7 |
| 35 | 20.0 | 16.8 | 34.5 | 28.4 |
| 37 | 20.6 | 18.5 | 34.2 | 27.2 |
| 39 | 18.0 | 15.8 | 33.1 | 24.4 |
| 42 | 19.2 | 15.1 | 31.9 | 24.1 |
| 43 | 23.9 | 20.7 | 32.1 | 22.0 |
| 60 | 20.7 | 16.3 | 32.4 | 20.3 |
| 64 | 22.3 | 16.1 | 30.0 | 23.0 |
| 71 | 21.8 | 20.9 | 33.1 | 24.7 |
| 76 | 22.8 | 21.5 | 28.5 | 25.0 |
| 81 | 16.5 | 16.0 | 29.1 | 22.7 |
| 92 | 15.3 | 15.0 | 30.3 | 23.5 |
| Control/Mean[6] | 19.7 | 16.8 | 31.0 | 25.1 |

[1]Four central strips were cut from each of 4–6 tubers and fried at 375° F.
[2]Reflectance measurements were taken using a PHOTOVOLT 577 Reflectance meter.
[3]Strips were prepared from field-grown tubers that had been stored at 50 ° F. for 1 month and then at 40° F. for 4 months (cold storage)
[4]Strips were prepared from field-grown tubers that had been stored at 50 ° F. for 1 month and at 40° F. for 4 months (cold storage), and subsequently reconditioned at 55° F. for 21 days.
[5]Reflectance was measured separately on bud and stem ends of fried strips.
[6]The mean values for 22 control Russet Burbank lines are presented for comparison.

From the foregoing, it will be seen that this invention is one well adapted to attain all the ends and objects hereinabove set forth together with advantages which are obvious and which are inherent to the invention. It will be understood that certain features and subcombinations are of utility and may be employed without reference to other features and subcombinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

REFERENCES

Anderson, et al. (1989a) J. Biol. Chem. 264 (21):12238–12242.
Anderson, et al. (1989b) First International Symposium on the Molecular Biology of the Potato, Bar Harbor, Me. ap Rees, et al. (1988) Syrup. Soc. Exp. Biol. 42: 377–393.
Baker, S.S., et al. (1994) Plant Mol. Biol. 24:701–713.
Barker, et al. (1983) Plant Mol. Biol. 2:335–350.
Bevan, et al. (1983) Nature (London) 304:184–187.
Bevan, et al. (1986) Nucleic Acids Res. 14 (11):4625–4638.
Bhave, et al. (1990) Plant Cell 2: 581–588.
Birnboim, et al. (1979) Nucleic Acids Res. 7:1513–1523.
Blennow, et al. (1991) Phytochemistry 30:437–444.
Burton, W. G. (1989) The Potato. Longman Scientific and Technical, Harlow, England, pp 865–522
Cattaneo, et al. (1969) Biochem. Biophys. Res. Commun. 34 (5):694–701.
Chang, et al. (1978) J. Bacteriol. 134; 1141–1156.
Claassen, et al. (1991)Plant Physiol. 95:1243–1249
Coffin, et al. (1987) J. Food Sci. 52: 639–645.
Copeland, L. and J. Preiss (1981) Plant Physiol. 68: 996–1001.
Coruzzi, et al. (1984) EMBO J. 3(8): 1671–1679.
Creuzet-Sigal, et al. (1972) "Genetic Analysis and Biochemical Characterization of Mutants Impairing Glycogen Metabolism in Escherichia coli K12" in Biochemistry of the Glycosidic Linkage: An Integrated View. Edited by R. Piras and H. G. Pontis. 647–680. New York: Academic Press Inc.
Dickinson, D. B. and J. Preiss (1969) Plant Physiol. 44:1058–1062.
Ditta, et al. (1980) Proc Natl Acad Sci USA 77, 7347–7351.
Dixon, et al. (1981) Phytochemistry 20: 969–972.
du Jardin, P. and Berhin, A. (1991) Plant Mol. Biol. 16:349–351.
Ebbelaar, et al. (1993) Int. Syrup. on Gen. Manip. of Plant Metabolism and Growth, 29–31 March, Norwich UKAbstract #9.
Ehrlich, H. A. (1989)Ed. PCR Technology—Principles and Apnlications for DNA Amplification. Stockton Press, New York.
Fling, et al. (1985) Nucleic Acids Research 13 no. 19, 7095–7106.
Fraley, et al. (1983) Proc Natl Acad Sci USA 80, 4803–4807.
Fraley, et al. (1985) Bio/Technology 3, 629–635.
Frohman, M. A. (1990) In: PCR Protocols. Innis, M. A., Gelfand, D. H., Snincky, J. J., and White, T. J., eds. Academic Press, San Diego, Calif. pp. 28–38.
Frohman, et al. (1988) Proc. Natl. Acad. Sci. USA 85: 8998–9002.
Ghosh, et al. (1966) J. Biol. Chem. 241 (19):4491–4504.
Gilmour, et al. (1992) Plant Mol. Biol. 18:13–21.
Hajela, et al. (1990) Plant Physiol. 93:1246–1252.
Hannapel, D. J. (1990) Plant Physiol. 94: 919–925.
Hardenburg, et al. (1986) USDA Agric. Handbook No 66, pp 66–68
Haugen, et al (1976) J. Biol. Chem. 251. (24) 7880–7885
Heldt, et al. (1977) Plant Physiol. 59: 1146–1155.
Houde, et al. (1992) Plant Physiol. 99(4):1381–1387.
Huang, R.C., et al. (1987) FED Proc. 46 (6): 2238.
Iglesias, et al., (1993) J. Biol Chem. 268:1081–1086.
Jarret, et al. (1980a) Physiol. Plant. 49: 177–184.
Jarret, et al. (1980b) J. Amer. Soc. Hort. Sci. 105: 238–242.
Jarret, et al. (1981) In Vitro 17: 825–830.
Jefferson, et al. 1990. Plant Mol. Biol. 14: 995–1006.
Kaiser, W. M. and J. A. Bassham (1979) Plant Physiol. 63: 109–113.
Kay, et al. (1987) Science 236:1299–1302.
Koncz, C. and Schell, J. (1986) Mol. Gen. Genet. 204:383–396.
Kossmann et al. (1991) Mol. Gem Genet. 230:39–44.
Krishnan, et al (1986) Plant Physiol. 81: 642–645.
Kruger, N. J. and Hammond, J. B. W. (1988) Plant Physiol. 86: 645–648.
Kurkela, et al. (1990) Plant Mol. Biol. 15:137–144.
Laemmli, U. K. (1970) Nature (London) 227:680–685.
Leung, et al. (1986) J. Bact. 167 (1):82–88.
Lin, et al. (1988a) Plant Physiol. 86:1131–1135.
Lin, et al. (1988b) Plant Physiol. 88:1175–1181.
Liu, X. J., et al. (1990) Mol. Gen. Genet. 223:401–406.

Lob, et al. (1989) Science 243:217–220.
Lutcke et al. (1987) EMBO J. 6(1):43–48.
Mignery, et al. (1988) Gene Gene 62:27–44.
Miller, J. H. (1972) Experiments in Molecular Genetics. Cold Spring Harbor Laboratory, Cold Spring Harbor, N.Y.
Miner, et al. (1992) J. Neurosci. Res. 33(1): 10–18.
Morell, et al. (1988) J. Biol. Chem. 263:633–637.
Morell, et al. (1987) Plant Physiol. 85:182–187.
Mori et al. (1991) J. Biol. Chem. 266: 18446–18453.
Muller, et al. (1990) Mol. Gen. Genet. 224:136–146.
Murata, et al. (1992) Nature 356:710–713.
Nakano et al. (1989) J. Blochem. 106: 691–695.
Nakata, et al. (1992) J. Cell. Biochem. Suppl. 16F, Abst. Y311, p.266.
Nordin, K, et al. (1993) Plant Mol. Biol. 21: 641–653.
Odell, et al. (1985) Nature 313,810–812.
Ohta et al. (1991) Mol. Gen. Genet. 225: 369–378.
Okita, et al. (1990) 93: 785–790.
Olive, et al. (1989) Plant Mol. Biol. 12: 525–538.
Plaxton, et al. (1987) Plant Physiol. 83: 105–112.
Preiss, Jack. (1988) "Biosynthesis of Starch and Its Regulation" in *The Biochemistry of Plants*. Edited by J. Preiss. 184–249. Orlando, Fla.: Academic Press.
Preiss, et al. (1971) Biochem. Biophys. Res. Comm. 42:180–186.
Pressey, R. (1966)Arch. Biochem. Biophys. 113: 667–674.
Qoronfieh, et al. (1992)J. Bacteriol. 174(24): 7902–7909.
Rocha-Sosa, et al. (1989) EMBO J. 8(1):23–29.
Rohde et al., (1990) J. Genet. & Breed. 44:311–315.
Ryall, A. L. and Lipton, W. J. (1979) Vegetables and Melons, Vol. 1. AVI, Westport, Conn., pp 225–230, 272–279.
Sambrook, et al. (1989) Molecular Cloning, A Laboratory Manual. 2nd Ed. Cold Spring Harbor Laboratory Press, N.Y.
Santarius, et al. (1965) Biochim. Biophys. Acta 102:39–54.
Shahar et al. (1992) Plant Cell 4:135–147.
Shallenberger, et al. (1959) Agric. and Food Chem. 7: 274–277.
Smith-White, B. and J. Preiss (1992) J. Mol. Evol. 34:449–464.
Solanoubat, M. and G. Belllard (1987) Geneg 60:47–56.
Solanoubat, M. and G. Belllard (1989) Geneg 84:181–185.
Sowokinos, J. R., and J. Preiss. (1982) Plant Physiol. 69:1459–1466.
Stalker, et al (1981) Mol Gert Genet 181, 8–12.
Stiekema et al. (1988) Plant Mol. Biol. 11: 255–269.
Stukerlj et al. (1990) Nucl. Acids Res. 18:46050.
Svab, et al. (1990) Proc. Natl. Acad. Sci. USA 87:8526–8530.
Takaha et al., (1993) J. Biol. Chem. 26 8:1391–1396.
Timko, et al. (1985) Nature (London) 318: 579–582.
Tsai, C. Y. and O. E. Nelson. (1966) Science 151: 341–343.
Vasil, V., F. Redway and I. Vasil. (1990) Bio/Technology 8:429–434.
van Berkel, J., et al. (1991) Abstract #1576 presented at the International Congress of Plant Molecular Biology, Tucson, Ariz.
van Berkel, J., et al. (1994) Plant Physiol. 104: 445–452.
Von Scheele, C. (1937) Landw Ver Stn 127: 67–96.
Weaver, et al. (1978) Am. Pot. J. 55:83–93.
White, T. C., et al. (1992) Plant Physiol. 99 (Suppl. 1):78.
Wilhelm, K. S., et al. (1993) Plant Mol. Biol. 23: 1073–1077.
Wong, et al. (1988) Geneg 68: 193–203.
Yamaguchi-Shinozaki, et al. (1993) Mol. Gem Genet. 238:331–340.
Yamaguchi-Shinozaki, K. and Shinozaki, K. (1994) The Plant Cell 6: 251–264.
Yoshida et al. (1992) Geneg 10: 255–259.
Zhu, B., et al. (1993) Plant Mol. Biol. 21: 729–735.

We claim:

1. A method of reducing the level of sugars within potato tubers stored at reduced temperatures comprising providing an increased level of ADPglucose pyrophosphorylase enzyme activity during storage at reduced temperatures by transforming potato plants with a recombinant, double-stranded DNA molecule comprising (a) a promoter which functions in potato tubers to cause the production of an RNA sequence in tubers, (b) a structural DNA sequence that causes the production of an RNA sequence which encodes a fusion polypeptide comprising an amino-terminal plastid transit peptide and a foreign ADPglucose pyrophosphorylase enzyme, and (c) a 3' nontranslated DNA sequence which functions in plant cells to cause transcriptional termination and the addition of polyadenylated nucleotides to the 3' end of the RNA sequence; obtaining tubers from such transformed potato plants; and storing said tubers at reduced temperatures without formation of unacceptably high sugar levels.

2. The method of claim 1 wherein said ADPGPP enzyme is the E. coli glgC enzyme.

3. The method of claim 1 wherein said ADPGPP enzyme is a mutant E. coli enzyme.

4. The method of claim 3 wherein said ADPGPP enzyme has the sequence shown in SEQ ID NO:4.

5. A method of prolonging dormancy of stored potato tubers comprising providing an increased level of ADPglucose pyrophosphorylase enzyme activity within the tuber during storage by transforming potato plants with a recombinant, double-stranded DNA molecule comprising (a) a promoter which functions in potatoes to cause the production of an RNA sequence in tubers, (b) a structural DNA sequence that causes the production of an RNA sequence which encodes a fusion polypeptide comprising an amino-terminal plastid transit peptide and a foreign ADP-glucose pyrophosphorylase enzyme, and (c) a 3' nontranslated DNA sequence which functions in plant cells to cause transcriptional termination and the addition of polyadenylated nucleotides to the 3' end of the RNA sequence; and obtaining tubers from such transformed potato plants which exhibit inhibited sprouting during storage.

6. The method of claim 5 wherein said storage is at reduced temperatures.

7. The method of claim 6 wherein said ADPGPP enzyme is the E. coli glgC16 enzyme.

8. The method of claim 6 wherein said ADPGPP enzyme has the sequence shown in SEQ ID NO:4.

* * * * *